United States Patent
Arai et al.

(10) Patent No.: US 6,346,075 B1
(45) Date of Patent: Feb. 12, 2002

(54) AIR AND WATER SUPPLY VALVE STRUCTURE IN ENDOSCOPE

(75) Inventors: Kaoru Arai; Hiroshi Kuboya; Mitsuo Kondo, all of Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/492,836

(22) Filed: Jan. 27, 2000

(30) Foreign Application Priority Data

Feb. 1, 1999 (JP) ............................................. 11-024104
Sep. 14, 1999 (JP) ............................................. 11-260744
Sep. 14, 1999 (JP) ............................................. 11-260746

(51) Int. Cl.[7] ............................................. A61B 1/015
(52) U.S. Cl. ............................................. 600/159
(58) Field of Search ........................ 600/159; 251/186, 251/190; 137/538, 625.67, 625.68

(56) References Cited

U.S. PATENT DOCUMENTS 4,361,138 A * 11/1982 Kinoshita ................... 600/159
4,852,551 A * 8/1989 Opie et al. ................... 600/121
5,027,791 A * 7/1991 Takahashi ................... 600/158
5,301,656 A * 4/1994 Negoro et al. ............... 600/149
5,347,992 A * 9/1994 Pearlman et al. ............ 600/131
5,938,589 A * 8/1999 Wako et al. ................. 600/159

* cited by examiner

*Primary Examiner*—Linda C. M. Dvorak
*Assistant Examiner*—Jocelyn Ram

(57) ABSTRACT

A piston of an air and water supply valve in an endoscope comprises: a base cylinder; a water supply switching piston; and an air supply switching piston, which is inserted in the water supply switching piston. An air supply button functioning as a check valve is attached to the top end of the air supply switching piston, and air is supplied by slightly pressing the air supply button and water is supplied by deeply pressing the air supply button. If liquid flows back, the air supply button functions as the check valve to prevent the backflow from flowing into the base cylinder from the air supply switching piston.

8 Claims, 29 Drawing Sheets

F I G. 4
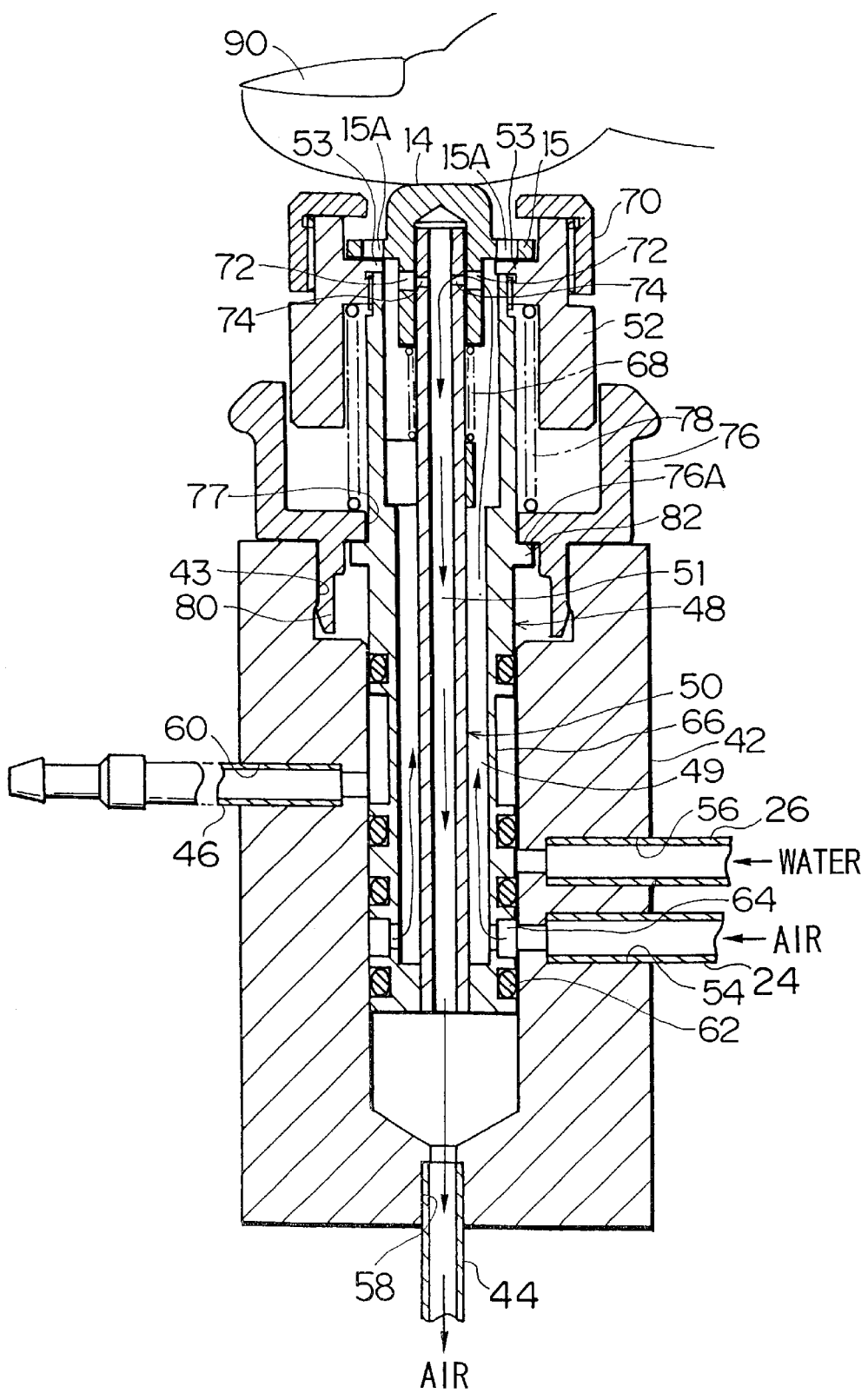

F I G. 2 3
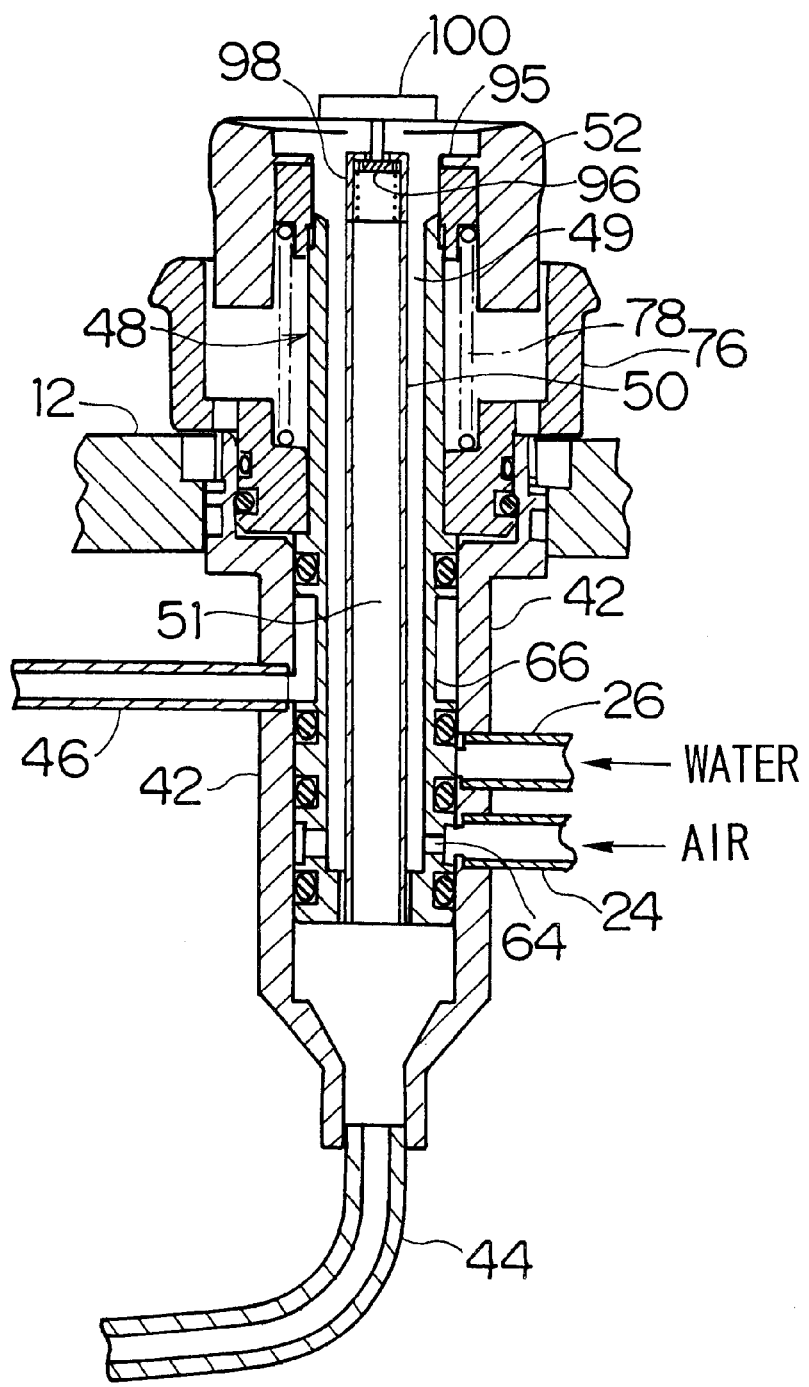

AIR AND WATER SUPPLY VALVE STRUCTURE IN ENDOSCOPE

BACKGROUND OF THE INVENTION

1. Field of the Invention

This invention relates generally to an air and water supply valve structure in an endoscope. More particularly, this invention relates to an air and water supply valve structure for alternatively supplying air or water into a body cavity or the like, in an endoscope for medical use.

2. Description of Related Art

An air and water supply valve structure is provided at a manual operation part of an endoscope for medical use. If an operator operates the air and water supply valve with fingers, air or water is alternatively supplied into a body cavity.

A conventional air and water supply valve structure comprises a cylinder, a piston and operation members such as buttons. The cylinder is fixed at a predetermined position of the manual operation part, and the piston is slidably inserted into the cylinder. An air supply button is attached to the top of the piston. If the operator closes an air leak opening of the air supply button, the air in the cylinder is supplied into the body cavity through an air supply tube. If the piston is pressed down by operating a water supply button, the supply of the air is stopped and the water in the cylinder is supplied into the body cavity through a water supply tube.

The conventional air and water supply valve structure has a check valve on the air supply tube. The check valve prevents a liquid in the body cavity from flowing back into the cylinder through the air supply tube, and thus prevents the liquid from contaminating the cylinder and the like. In the conventional air and water supply valve structure, however, the resistance of the check valve on the air supply tube increases a pressure loss in the air supply, and this necessitates, an air source that is able to overcome the resistance. This substantially increases the consumption of energy. Moreover, in the conventional air and water supply valve, the check valve makes it difficult to clean the air supply tube.

The cylinder and the piston have circular openings connected to air supply passages. When the positions of the openings are matched to one another, the air supply passages are connected to one another through the openings to supply the air. If the piston is slid to bring the openings out of line, the air supply passages are disconnected and the supply of the air is stopped.

The conventional valve structure, however, cannot achieve the satisfactory airtightness of the valve when the air supply passage is blocked. In order to improve the airtightness of the conventional structure, the openings must be much brought out of line, and the stroke length of the piston must be a large amount. If the stroke length of the piston is designed to be large, however, an operator must deeply press the air supply button and this makes it difficult to operate the valve. For this reason, it is unpreferable to increase the stroke length of the piston, and thus, the conventional valve structure cannot improve the airtightness of the valve.

SUMMARY OF THE INVENTION

It is therefore an object of the present invention to provide an air and water supply valve structure in an endoscope that functions as a check valve without a special check valve and reduces a pressure loss in air supply to the minimum. Another object of the present invention is to provide a valve structure, which improves the airtightness of the valve without increasing the stroke length of a piston.

In view of the foregoing, it is an object of the present invention to provide an air and water supply valve structure provided at a manual operation part of an endoscope, comprising: a base cylinder that is a hollow cylinder connecting: to an air feed tube feeding air into the base cylinder, to a water feed tube feeding water into the base cylinder, to an air supply tube to supply the air from the base cylinder to an air and water supply opening formed at an end of an insertion part of the endoscope, and to a water supply tube to supply the water from the base cylinder to the air and water supply opening; a first piston that is a hollow cylinder slidably inserted into the base cylinder, the first piston having a connection opening to connect the air feed tube and an inner space of the first piston, the first piston having a connection passage to connect the water feed tube and the water supply tube; a second piston that is a hollow cylinder arranged inside the first piston, an inner space of the second piston being connected to the air supply tube; a first operation member provided to the second piston, the first operation member being pressed by first and second steps, the first operation member connecting, when pressed by the first step, the inner space of the first piston and the inner space of the second piston, and the first operation member disconnecting, when not pressed, the inner space of the first piston and the inner space of the second piston; and a second operation member provided to the first piston, wherein when the first operation member is pressed by the second step, the second operation member is pressed and positions the first piston such that the connection opening of the first piston is disconnected from the air feed tube and that the connection passage of the first piston connects the water feed tube and the water supply tube.

According to the present invention, if the first operation member is pressed by the first step, the inner space of the first piston connects to the inner space of the second piston, and thus, the air fed into the inner space of the first piston is supplied to the air supply tube through the inner space of the second piston. Consequently, the air is supplied into the body cavity.

If the first operation member is pressed by the second step, the second operation member operated by this operation positions the first piston at such a position that the connection opening of the first piston can be withdrawn from the air feed tube, and this stops the supply of the air and that the connection passage of the first piston can connect the water feed tube and the water supply tube. Consequently, the water is supplied into the body cavity. The air is switched to the water in this manner. In short, if the connection opening of the first piston is withdrawn from the air feed tube, the air is supplied from the air feed tube to a water tank. This raises the inner pressure of the water tank, so that the water is supplied from the water tank into the water feed tube.

When the air is supplied by pressing the first operation member by the first step, the inner pressure of the air supply tube is higher than that of the body cavity. For this reason, the liquid in the body cavity never flows back into the air and water supply valve through the air supply tube. If, however, the inner pressure of the body cavity is higher than the inner pressure of the air supply tube when the first operation member is not operated, the backflow flows into the inner space of the second piston through the air supply tube. At this time, however, the inner space of the first piston and the inner space of. the second piston are unconnected since the first operation member is not operated. Thus, the backflow never flows into the inner space of the first piston, and does not contaminate the first piston and the base cylinder. In short, the air and water supply valve structure of the present invention has the first operation member functioning as a check valve, and this eliminates the necessity of a special check valve and reduces the pressure loss in the air supply to the minimum.

If a button is used in the first operation member, the inner space of the first piston and the inner space of the second piston are connected through a connection opening formed in the button when the button is pressed by the first step. Therefore, the air can flow smoothly without any resistance to the air supply tube, and this reduces the pressure loss in the air supply to the minimum.

If an elastic member is used in the first operation member, a cut groove formed in the elastic member is opened when the elastic member is squashed. Consequently, the inner space of the first piston is connected to the inner space of the second piston through the open cut groove. Therefore, the air can flow smoothly without any resistance to the air supply tube, and this reduces the pressure loss in the air supply to the minimum.

If a spiral spring whose adjacent spirals are in close contact with one another is used in the first operation member, the inner space of the first piston and the inner space of the second piston are connected through gaps formed between the spirals when the spiral spring is buckled. Therefore, the air flows into the air supply tube without any resistance, and this reduces the pressure loss in the air supply to the minimum.

If a shutter plate is used in the first operation member, an opening for connecting the inner space of the first piston and the inner space of the second piston is opened when a pressing member presses the shutter plate against the force of a forcing member. Consequently, the inner spaces of the first and second pistons are connected. Therefore, the air can flow smoothly without any resistance to the air supply tube, and this reduces the pressure loss in the air supply to the minimum.

Preferably, the air supply tube and the water supply tube are straight over predetermined lengths, respectively, so that a cleaning brush can easily be inserted into them. Thus, the air supply tube and the water supply tube can be cleaned easily. More preferably, the air supply tube is straight and arranged parallel to an axial direction of the base cylinder over a predetermined length and has a mouth thereof within an inner diameter of the base cylinder, so that the cleaning brush can easily be inserted from cylinder into the air supply tube. Thus, the air supply tube can be cleaned easily.

To achieve the above mentioned object, the present invention provides a valve structure in an endoscope, comprising: a first member having a first passage for a fluid, the first passage having a first opening; and a second member having a second passage for the fluid, the second passage having a second opening; wherein the first and second members are slidable with respect to one another in a sliding direction, the first and second passages are connected through the first and second openings when the first and second openings are faced to one another, the first and second passages are disconnected when the first and second openings are not faced to one another, and at least one of the first and second openings has a length thereof in the sliding direction being shorter than a length thereof in a direction perpendicular to the sliding direction.

According to the present invention, the opening of at least one of the two slidable members of the valve has a shorter side in the sliding direction and has a longer side in the direction perpendicular to the sliding direction. For example, the opening is an oblong with a longer side in the sliding direction and a shorter side in the perpendicular direction, or an oval with a shorter diameter in the sliding direction and a longer diameter in the perpendicular direction. Therefore, the length in the sliding direction can be reduced without reducing an opening area, more specifically a fluid passage area. This increases an interval between the openings out of line. It is therefore possible to improve, without changing the stroke length of the piston, the airtightness of the valve when the passages are unconnected.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 4 is a sectional view showing a state wherein an air supply button of the air and water supply valve structure in FIG. 3 is pressed by the first step;

FIG. 23 is a sectional view showing the structure of an air and water supply valve structure according to the fourth embodiment;

DETAILED DESCRIPTION OF THE PREFERRED EMBODIMENT

This invention will be described in further detail by way of example with reference to the accompanying drawings.

Figure 1:
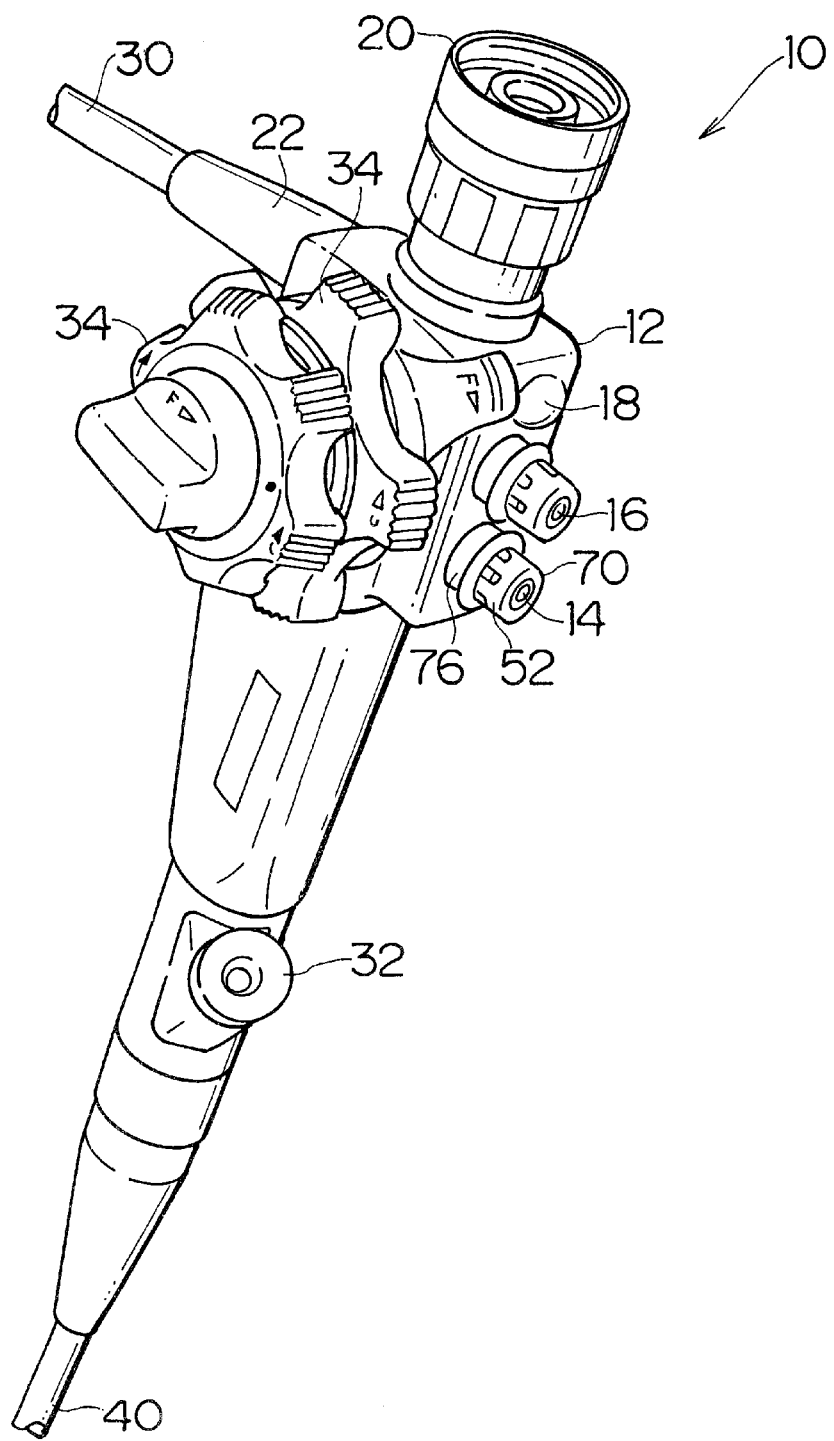
FIG. 1 is a perspective view showing an endoscope manual operation part, to which an air and water supply valve structure according to the present invention is applied.
Figure 2:
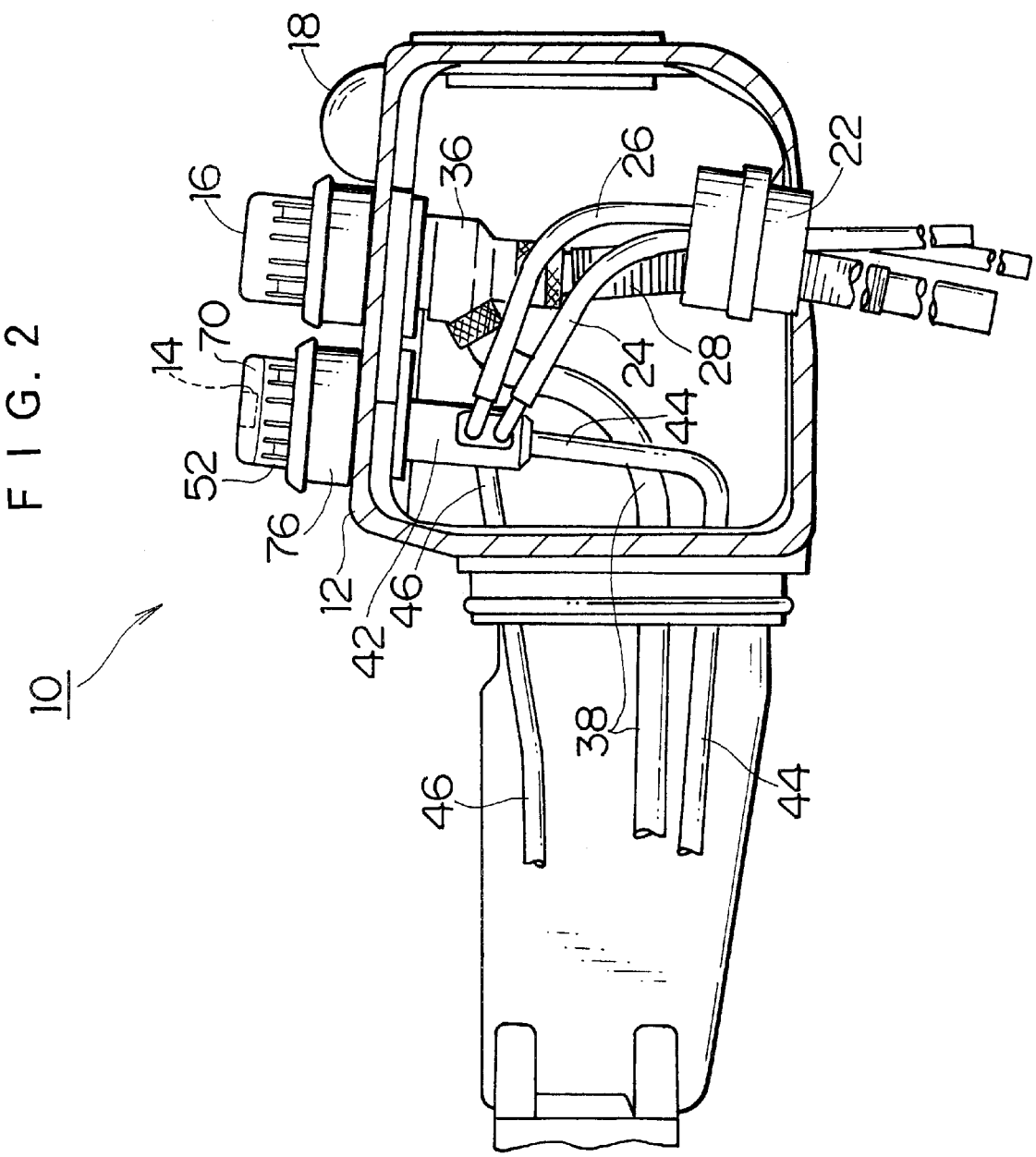
FIG. 2 is an internal view showing the endoscope manual operation part in FIG. 1.

FIG. 1 is a perspective view showing the exterior of an endoscope manual operation part 10 to which an air and water supply valve structure according to the first embodiment of the present invention is applied, and FIG. 2 is an internal view showing the manual operation part 10.

A first operation member or an air supply button 14 in the air and water supply valve according to the first embodiment is provided on the top of a body casing 12 of the manual operation part 10 in FIGS. 1 and 2, and a suction button 16 and a shutter release button 18 are provided adjacently to the air supply button 14. As shown in FIG. 1, an eyepiece 20 is provided at a rear end of the body casing 12. A connector 22 connects to the bottom of the body casing 12, and a connecting tube 30 connects to the connector 22. The connecting tube 30 contains an air feed tube 24, a water feed tube 26, a suction tube 28 (see FIG. 2), a light guide cable (not illustrated) and the like. In FIG. 1, reference numeral 32 denotes a forceps entrance, and 34 is an angle knob.

The suction tube 28 in FIG. 2 connects to a cylinder 36 of a valve operated by the suction button 16, and the cylinder 36 connects to a suction tube 38. The suction tube 38 is inserted into an insertion part 40 in FIG. 1, and is connected to a suction port at a hard end (not illustrated) of the insertion part 40. A piston (not illustrated) is inserted into the cylinder 36 in FIG. 2, and the piston connects and disconnects the suction tube 28 and the suction tube 38. The suction button 16 is attached to the top end of the piston. A forcing member (not illustrated) forces the suction button 16 or the piston in such a direction as to disconnect the suction tube 28 and the suction tube 38. The suction tube 28 and the suction tube 38 are connected by pressing the suction button 16 against the force of the forcing member. Mucus, pus and the like in a body cavity are sucked through the suction port at the hard end, and is discharged to the outside of the manual operation part 10 through the suction tube 38 and the suction tube 28.

The ends of the air feed tube 24 and the water feed tube 26 connect to predetermined positions of a base cylinder 42 in a valve operated by the air supply button 14. The base ends of the air supply tube 44 and the air supply tube 46 connect to predetermined positions of the base cylinder 42. The base end of the air feed tube 24 connects to an air supply unit such as a blower (not illustrated). Driving the air supply unit supplies air into the base cylinder 42 through the air feed tube 24. The base end of the water feed tube 26 connects to a water supply tank (not illustrated). Pressing a water supply button 52 closes the air feed tube 24, and the air that has been stopped flowing in the air feed tube 24 is supplied to the water supply tank. This raises the inner pressure of the water supply tank, so that the water can be supplied from the water supply tank to the base cylinder 42 through the water feed tube 26.

The air supply tube 44 and the water supply tube 46 are straight over a predetermined length so as to be easily cleaned by a cleaning brush. The air supply tube 44 is straight and coaxial with the base cylinder 42 over a predetermined length, so that the air supply tube 44 can be cleaned easily by the cleaning brush inserted from the base cylinder 42. The air supply tube 44 should not always be arranged coaxially with the base cylinder 42, but it may be arranged anyhow so far as the axis thereof is parallel to the axis of the cylinder 41 and the mouth of the air supply tube 44 is arranged within the inner diameter of the base cylinder 42.

The ends of the air supply tube 44 and the water supply tube 46 connect to an air/water supply tube (not illustrated) in the manual operation part 10. The air/water supply tube is inserted into the insertion part 40 in FIG. 1, and connects to an air/water supply port (not illustrated) formed at the hard end of the insertion part 40.

Figure 3:
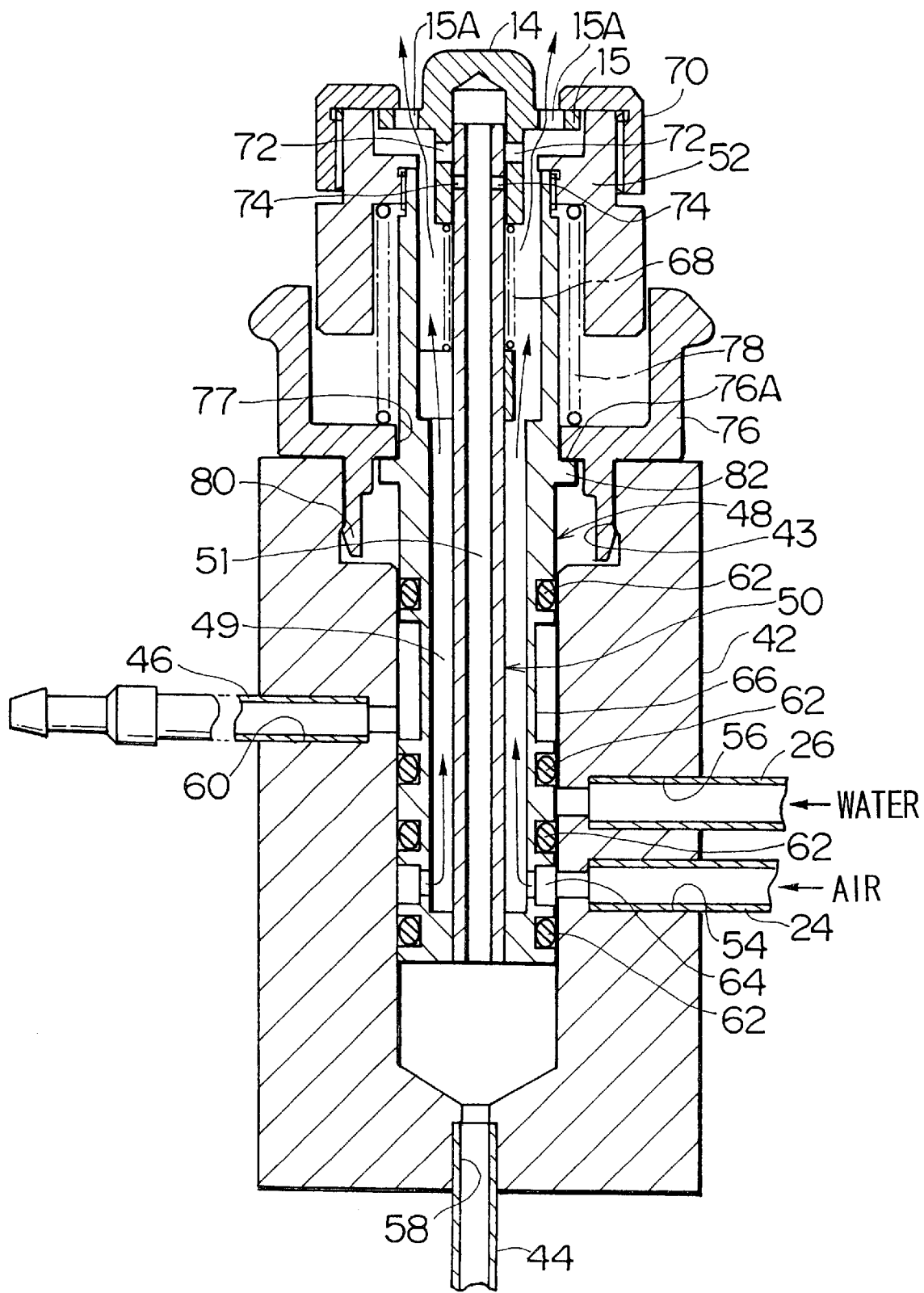
FIG. 3 is a sectional view showing the air and water supply valve structure according to the first embodiment of the present invention.

As shown in FIG. 3, the valve operated by the air supply button 14 comprises the base cylinder 42, a water supply switching piston (the first piston) 48, an air supply switching piston (the second piston) 50, the air supply button (the first operation member) 14 and the water supply button (the second operation member) 52.

The base cylinder 42 is fixed at a predetermined position in the body casing 12 in FIG. 2. As shown in FIG. 3, four ports 54, 56, 58, 60 are formed at the outer periphery and bottom of the base cylinder 42. The ports 54, 56, 58, 60 connect to the air feed tube 24, the water feed tube 26, the air supply tube 44 and the water supply tube 46, respectively.

The water supply switching piston 48 is cylindrical and inserted into the base cylinder 42 through a plurality of O-rings 62. The water supply switching piston 48 is detachable and vertically slidable with respect to the base cylinder 42. A connection opening 64 is formed at the lower part of the water supply switching piston 48, and is shaped like a groove along the outer circumference of the water supply switching piston 48. An inner space 49 of the water supply switching piston 48 connects with the port 54 through the connection opening 64 as shown in FIGS. 3 and 4. Consequently, the air supplied through the air feed tube 24 is sent into the inner space 49 through the connection opening 64.

Figure 5:
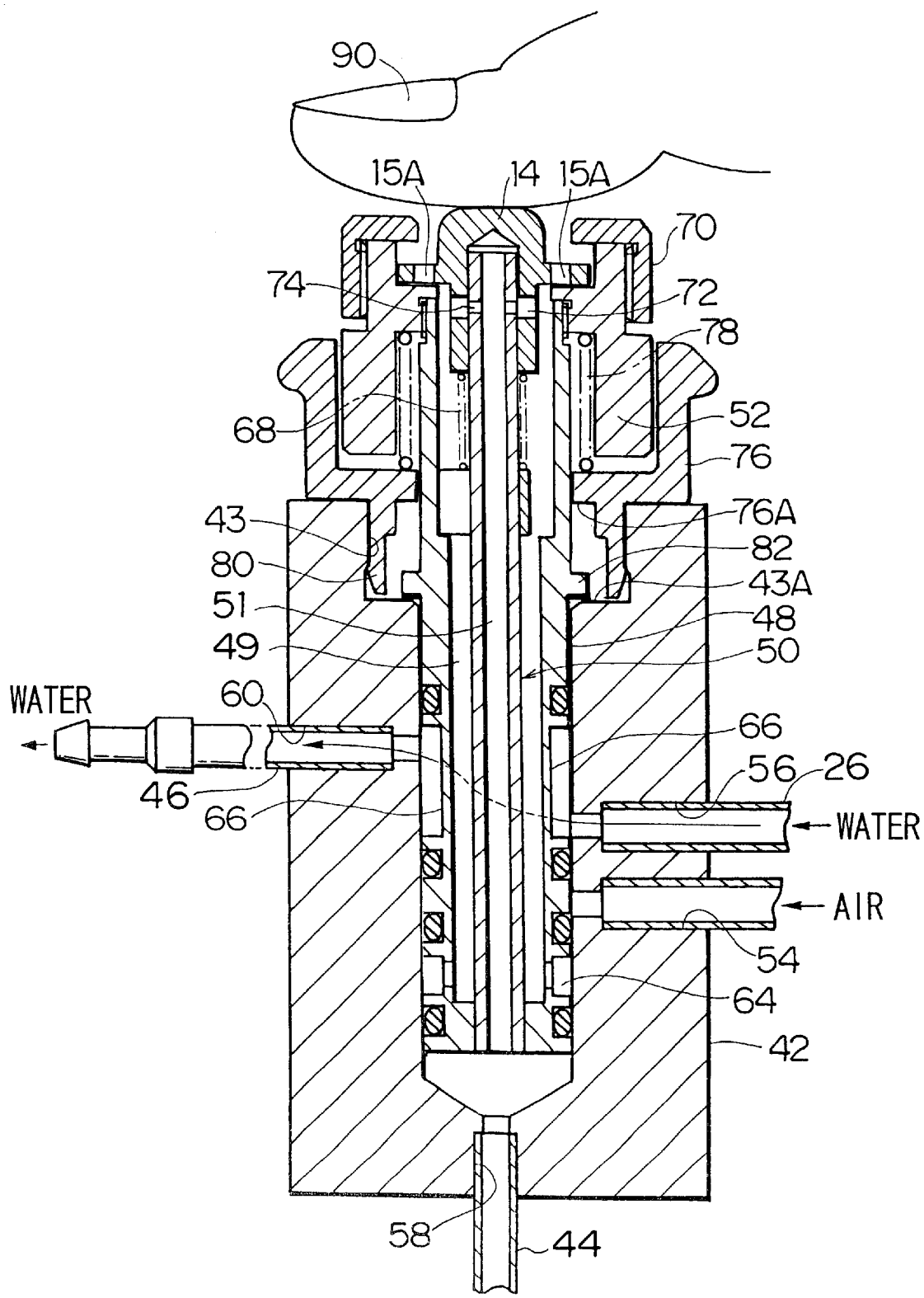
FIG. 5 is a sectional view showing a state wherein the air supply button of the air and water supply valve structure in FIG. 3 is pressed by the second step.

A connection passage or groove 66 is formed at substantially the center of the water supply switching piston 48 over the whole outer circumference. If the port 56 and the port 60 are connected with one another through the connection groove 66 as shown in FIG. 5, the water supplied through the water feed tube 26 is sent to the water supply tube 46 through the connection groove 66.

The air supply switching piston 50 is cylindrical and inserted into the inner space 49 of the water supply switching piston 48 coaxially with the water supply switching piston 48. The bottom end of the air supply switching piston 50 is fixed at the bottom end of the water supply switching piston 48, and the air supply button 14 is mounted at the top end of the air supply switching piston 50.

As shown in FIG. 3, the air supply button 14 is forced upward by a spring 68 arranged at the outer circumference of the air supply switching piston 50. A flange 15 is formed at the outer circumference of the air supply button 14, and is in contact with a cap 70 to prevent the air supply button 14 from jumping out due to the force of the spring 68. The flange 15 is provided with an air releasing opening 15A, through which the air sent into the inner space 49 is discharged to the outside.

The cap 70 is coupled onto the water supply button 52, which is coupled onto the water supply switching piston 48. The water supply button 52 is arranged in a substantially cylindrical button receiving member 76 through a spring 78, which has a spring constant larger than the spring 68. The button receiving member 76 is provided with an opening 77, through which the water supply switching piston 48 is arranged. A pawl 80 is formed at the button receiving member 76 and is elastically fitted in a top opening 43 of the base cylinder 42. A stopper flange 82 is formed on the outer periphery of the water supply switching piston 48. As shown in FIG. 5, the stopper flange 82 comes in contact with a bottom 43A of the top opening 43 of the base cylinder 42 when the water supply switching piston 48 is pressed. This regulates the press amount of the water supply switching piston 48. In FIGS. 3 and 4, the stopper flange 82 is pressed against a bottom 76A of the button receiving member 76. This prevents the water supply switching piston 48 from jumping out due to the force of the spring 78.

Thus, the water supply switching piston 48, the air supply switching piston 50, the air supply button 14, the cap 70, the water supply button 52 and the button receiving member 76 are handled as a united button unit. If the button receiving member 76 (or the cap 70 or the water supply button 52) is pulled up with fingers, the button unit as a whole can be pulled out of the base cylinder 42 in one operation. Consequently, the inside of the base cylinder 42 can be exposed and cleaned quickly.

Figure 6:
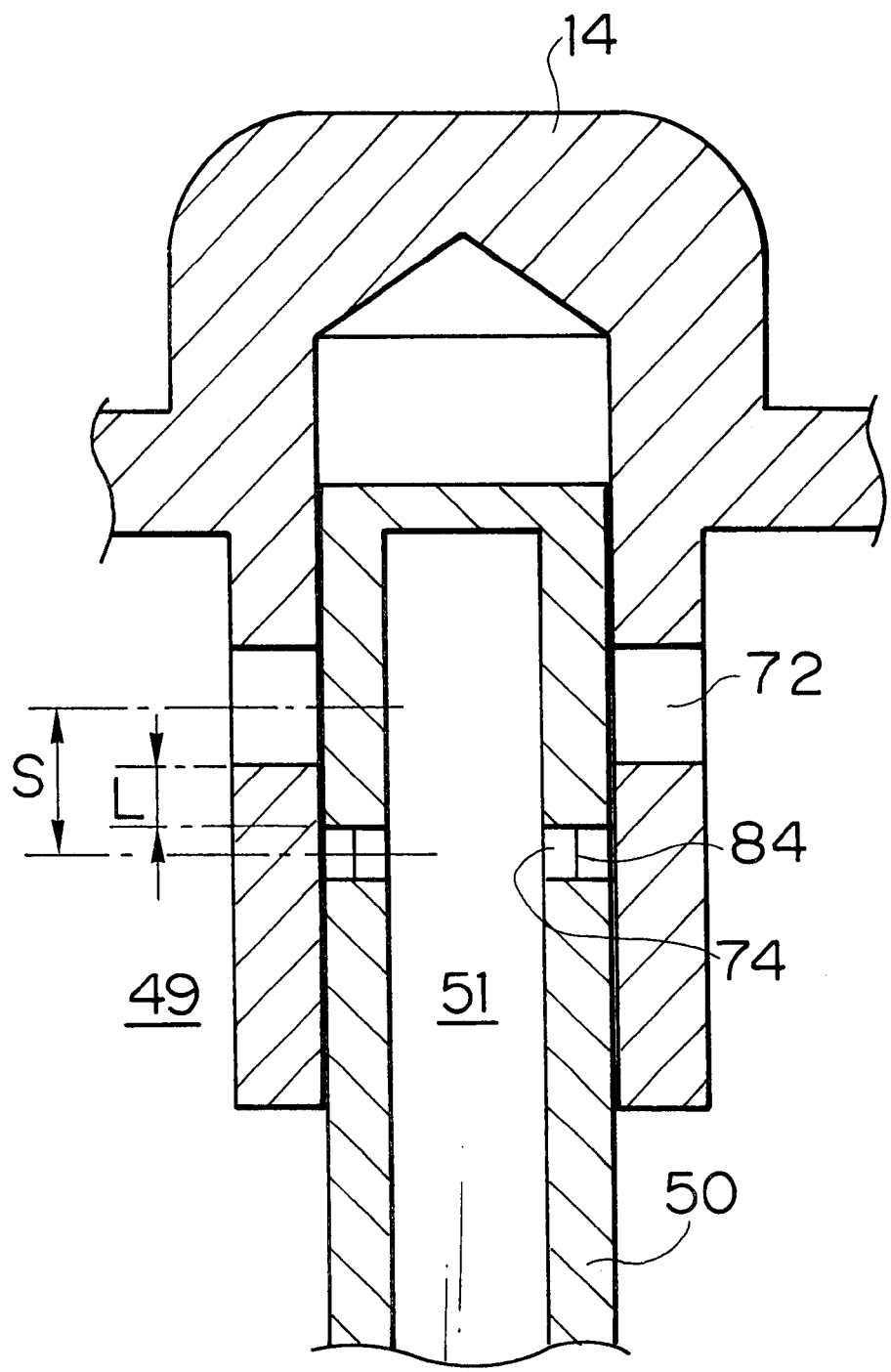
FIG. 6 is an enlarged sectional view showing the principal part of the air and water supply valve structure in the state in FIG. 3.
Figure 7:
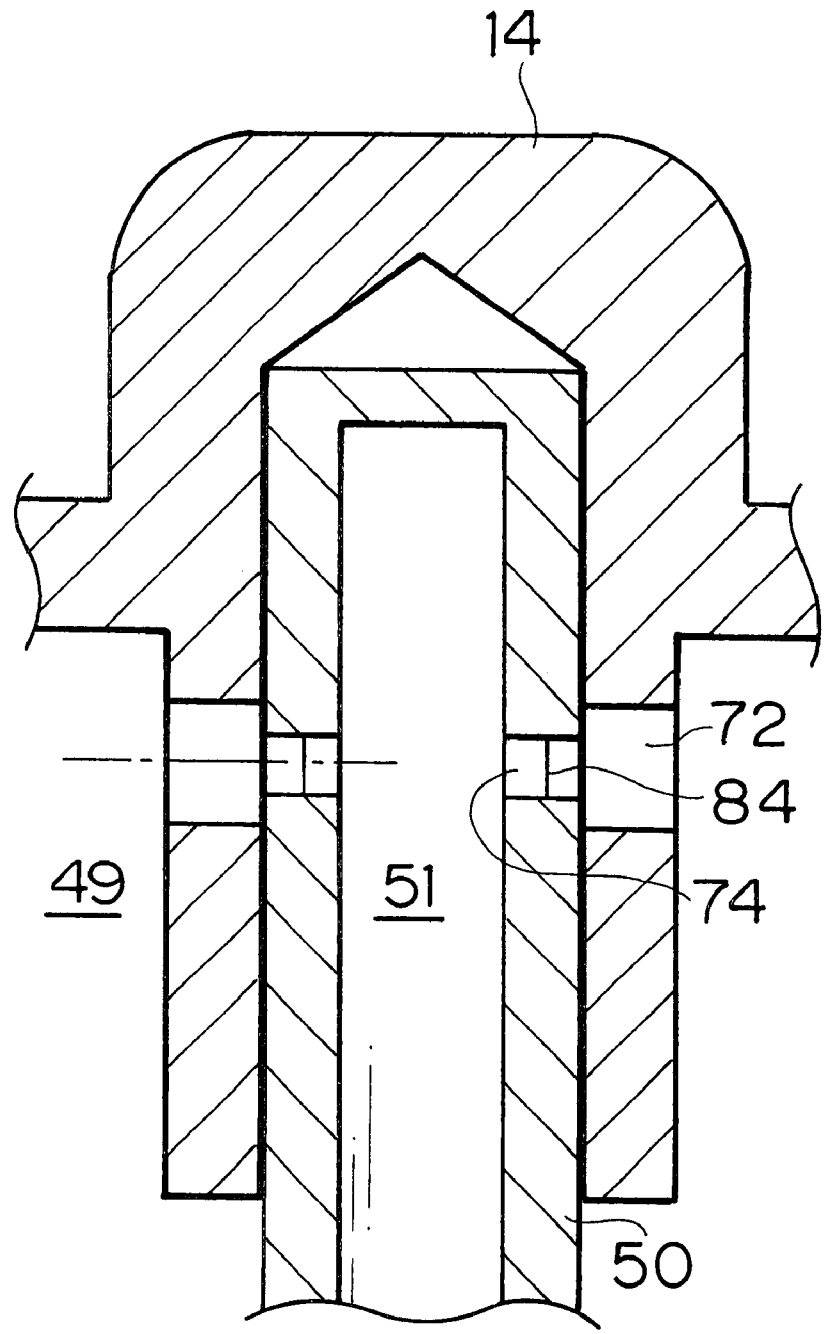
FIG. 7 is an enlarged sectional view showing the principal part of the air and water supply valve structure in the state in FIG. 4.
Figure 8:
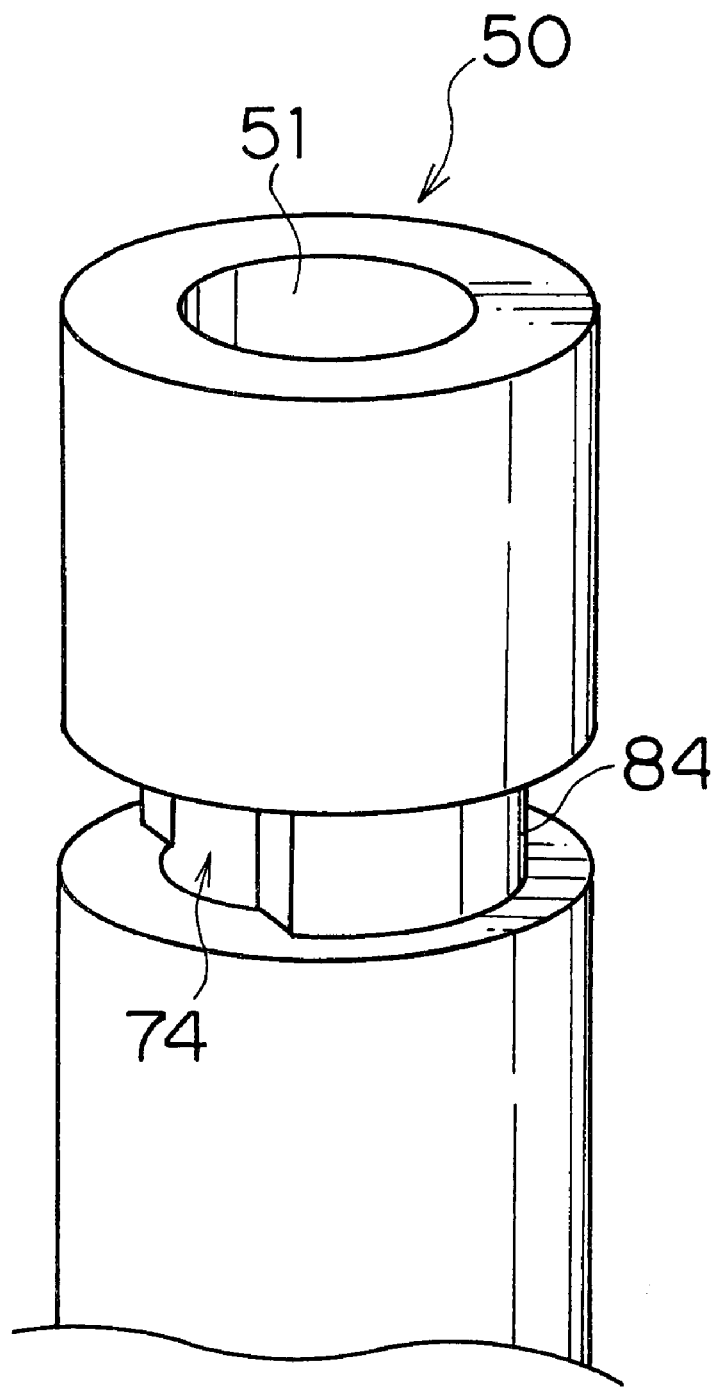
FIG. 8 is a perspective view showing an air supply switching piston of the air and water supply valve structure in FIG. 2.
Figure 9:
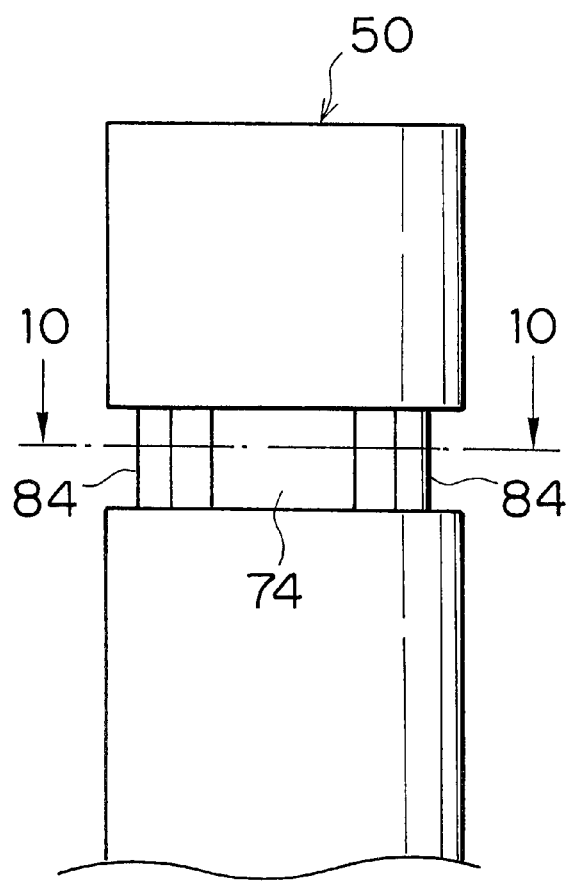
FIG. 9 is a side view of the air supply switching piston in FIG. 8.
Figure 10:
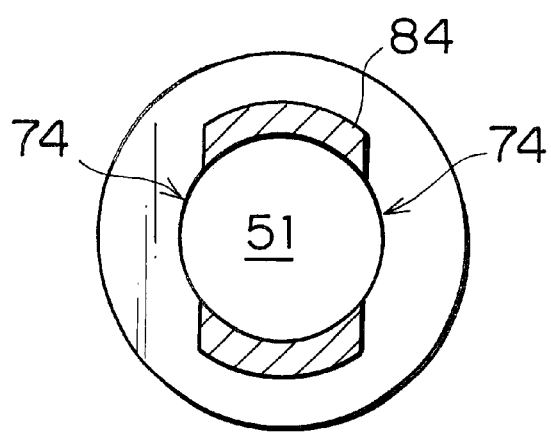
FIG. 10 is a sectional view of the air supply switching piston taken along line 10—10 in FIG. 9.

FIGS. 6 and 7 are enlarged sectional views of a part around the air supply button 14 corresponding to FIGS. 3 and 4, respectively. A couple of round connection openings 72 is formed at the circumference of the lower cylindrical part of the air supply button 14. A groove 84 is formed at the whole circumference of the upper position of the air supply switching piston 50, and a couple of connection openings 74 is formed in the groove 84. As shown in FIGS. 8–10, the connection openings 74 are formed by cutting off a couple of parts of the groove 84. For example, the connection openings 74 are formed by scraping away opposite sides of the groove 84 by milling. Consequently, the connection openings 74 are oblongs with the shorter sides along the axis of the air supply switching piston 50 (i.e., the sliding direction of the air supply switching piston 50), and the longer sides in a direction perpendicular to the axis of the air supply switching piston 50. Thus, the connection openings 74 are shorter in the axial direction than a circular opening with the same area.

If the air supply button 14 is pressed by a stroke length S from the state shown in FIGS. 3 and 6, the connection openings 72 are positioned to the same height as the groove 84 provided on the air supply switching piston 50 as shown in FIGS. 4 and 7. Thus, the inner space 49 and the inner space 51 are connected through the connection openings 72, the groove 84 and the connection openings 74 as shown in FIGS. 4 and 7. Consequently, the inner space 49 of the water supply switching piston 48 and the inner space 51 of the air supply switching piston 50 are connected in FIGS. 4, 5 and 7 in which the air supply button 14 is pressed. This enables the supply of the air.

In FIGS. 3 and 6, where the air supply button 14 is not pressed, the round connection openings 72 are located at higher positions than the groove 84. Therefore, the connection openings 72 are closed by the outer peripheral surface of the air supply switching piston 50, and the groove 84 is closed by the inner peripheral surface of the air supply button 14. This disconnects the inner space 49 of the water supply switching piston 48 and the inner space 51 of the air supply switching piston 50.

If the air supply button 14 is slightly pressed by the first step as shown in FIG. 4, the flange 15 of the air supply button 14 is pressed against an inner flange 53 of the water supply button 52. Consequently, the flange 53 closes the air releasing opening 15A. The air sent into the inner space 49 of the water supply switching piston 48 enters the inner space 51 of the air supply switching piston 50 through the connection openings 72 and the connection openings 74 without leaking through the air releasing opening 15A, and the air enters the air supply tube 44 through the port 58. According to the valve structure of the first embodiment, the air is thus supplied to the hard end of the insertion part by slightly pressing the air supply button 14 by the first step.

If the air supply button 14 is deeply pressed by the second step as shown in FIG. 5, the air releasing opening 15A is closed by the inner flange 53 as described with reference to FIG. 4, and the water supply switching piston 48 is pressed downward by the air supply button 14. For this reason, the port 54 is closed by the outer peripheral surface of the water supply switching piston 48, and the port 56 connects with the port 60 through the connection groove 66. This stops the supply of the air, and guides the water from the water feed tube 26 to the water supply tube 46 through the connection groove 66. According to the valve structure of the first embodiment, the water is thus supplied to the hard end of the insertion part by deeply pressing the air supply button 14 by the second step.

A description will now be given of the operation of the valve structure operated by the air supply button 14, which is constructed in the above-mentioned manner.

If a finger 90 of an operator slightly presses the air supply button 14 by the first step as shown in FIG. 4, the inner space 49 of the water supply switching piston 48 connects to the inner space 51 of the air supply switching piston 50 through the connection openings 72 and the connection openings 74.

Thus, the air supplied to the inner space 49 through the air feed tube 24 flows into the air supply tube 44 through the inner space 51 of the air supply switching piston 50. Consequently, the air can be supplied into the body cavity.

If the air supply button 14 is deeply pressed by the second step as shown in FIG. 5, the water supply button 52 is pressed down to press the water supply switching piston 48 in such a manner as to withdraw the connection opening 64 of the water supply switching piston 48 from the port 54. This stops the supply of the air. Then, the water supply switching piston 48 is positioned so that the connection groove 66 of the water supply switching piston 48 can connect the port 56 to the port 60. This causes the water to flow into the water supply tube 46. Consequently, the water is supplied into the body cavity.

If the inner pressure of the body cavity is higher than the inner pressure of the air supply tube 44 when the air supply button 14 is not pressed as shown in FIG. 3, liquid in the body cavity may flow into the base cylinder 42 through the air supply tube 44. In this case, the liquid flowing through the air supply tube 44 flows into the inner space 51 of the air supply switching piston 50. At this time, the inner space 49 of the water supply switching piston 48 and the inner space 51 of the air supply switching piston 50 are unconnected, since the air supply button 14 is not pressed. Therefore, the backflow cannot flow into the inner space 49 of the water supply switching piston 48, and the water supply switching piston 48 and the base cylinder 42 are thus prevented from being contaminated with the backflow. In short, the air supply button 14 in the valve structure of the first embodiment functions as a check valve, and this eliminates the necessity of providing a special check valve and reduces the pressure loss in the air supply to the minimum. The pressure generated by the backflow applies a force to the air supply button 14 in such a direction as to take the air supply button 14 off the air supply switching piston 50, but the air supply button 14 never comes off since it is supported by a stopper 70. Consequently, the inner spaces 49, 51 are completely disconnected.

In the first embodiment, the air supply tube 44 and the water supply tube 46 are straight by the predetermined lengths, and this facilitates the cleaning of the air supply tube 44 and the water supply tube 46 since the cleaning brush can easily be inserted into them.

In the state in FIG. 6 wherein the air supply button 14 is not pressed, the connection openings 72 are located at higher positions than the connection opening 74. Therefore, the connection openings 72 are closed by the outer peripheral surface of the air supply switching piston 50, and the connection opening 74 is closed by the inner peripheral surface of the air supply button 14. In this case, the airtightness of the inner space 49 and the inner space 51 depends on a distance L (hereinafter referred to as a fluid passage interval) between the connection opening 72 and the connection opening 74. The larger the fluid passage interval L is, the more the airtightness is improved. The increase in the fluid passage interval L would increase the stroke length S, and deteriorate the operability of the air supply button 14. For this reason, it is impossible to increase the stroke length. More particularly, the valve structure such as this embodiment cannot increase the stroke length S, since the air supply button 14 is pressed by two steps.

In the valve structure of this embodiment, the connection opening 74 is shorter in the sliding direction (i.e., a stroking direction), and the fluid passage interval L can be increased without increasing the stroke length S. This improves, without deteriorating the operability of the air supply button 14, the airtightness when the inner space 49 and the inner space 51 are unconnected.

As state above, the connection opening 74 is formed as an oblong with the shorter side in the sliding direction. This makes it possible to increase the fluid passage interval L without increasing the stroke length S, and improve the airtightness. This surely prevents the backflow when the inner space 49 and the inner space 51 are unconnected.

In this embodiment, the airtightness is improved by lengthening the fluid passage interval L with the stroke length S being maintained the same as that of the conventional structure. If, however, the fluid passage interval L is set to be the same length as that of the conventional structure, the stroke length S can be reduced to improve the operability of the air supply button 14. If the stroke length S and the fluid passage interval L are set to be the same as those of the conventional structure, in other words, if the length of the connection opening 74 in the sliding direction is set to be the same as that of the conventional structure, the length of the connection opening 74 in the direction perpendicular to the sliding direction can be longer than that of the conventional structure, and this increases the area of the connection opening 74. This broadens the fluid passage, so that the air can be supplied more steadily.

Figure 11:
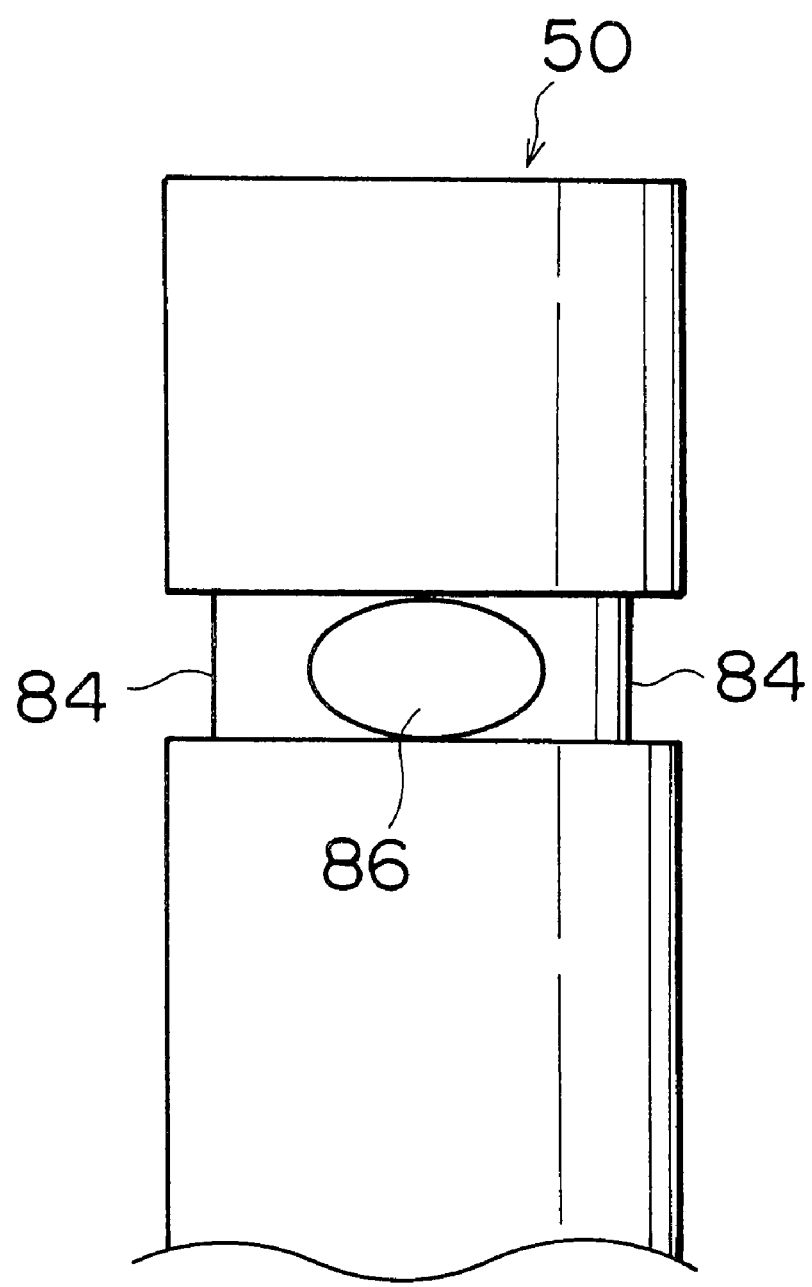
FIG. 11 is a side view showing an air supply switching piston with a connection opening of another shape.

The connection opening 74 is not necessarily rectangular, but it may take other forms on condition that it is long from side to side in such a way that the length of the connection opening 74 in the sliding direction of the air supply switching piston 50 is shorter than the length in the direction perpendicular to the sliding direction. Thus, an oval opening 86 with a shorter diameter in the sliding direction and a longer diameter in the perpendicular direction may be formed as shown in FIG. 11. The opening 86 is not necessarily elliptic, but the upper and lower sides of the opening 86 may be straight. A slit with a longer diameter in the perpendicular direction may be formed as the opening 74.

Figure 12:
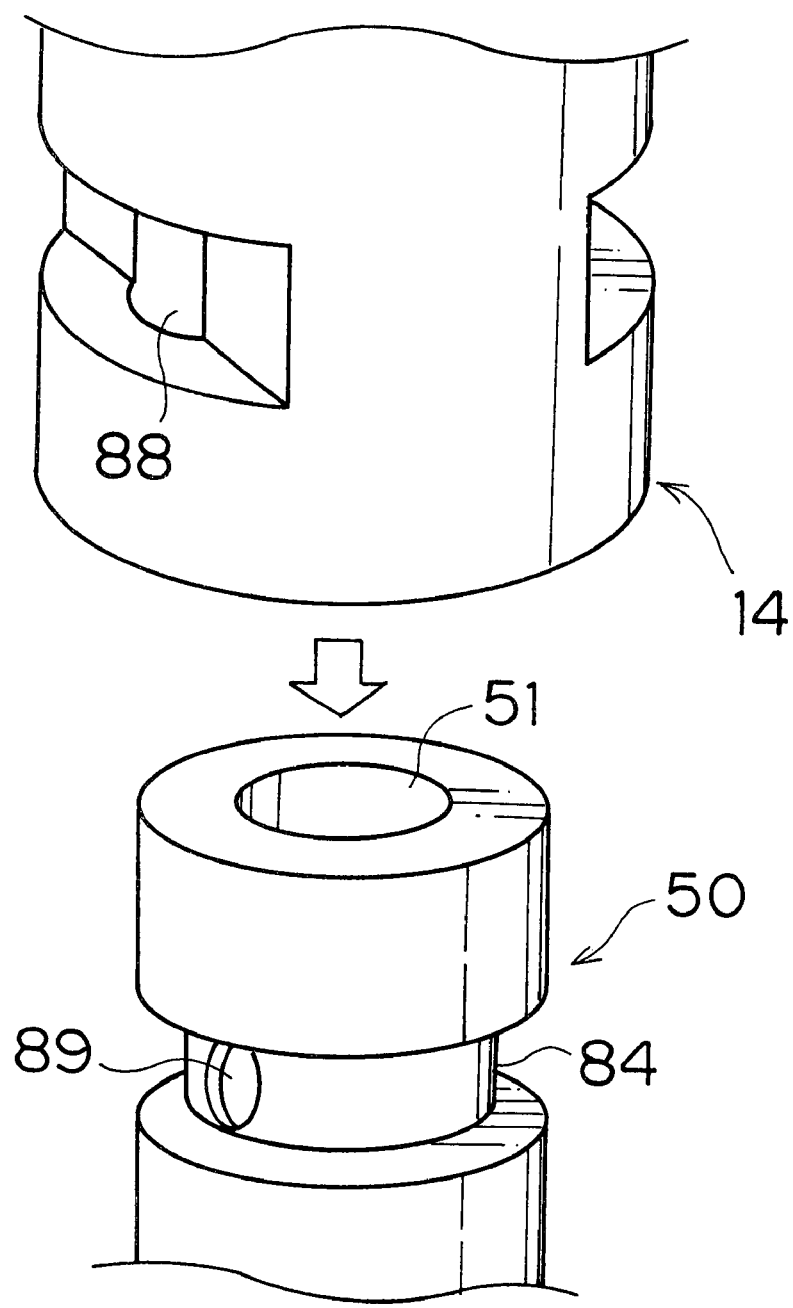
FIG. 12 is a perspective view showing another embodiment of an air supply button and an air supply switching piston.

In this embodiment, the connection opening 74 of the air supply switching piston 50 is long from side to side, but this invention should not be restricted to this. As shown in FIG. 12, an oblong connection opening 88 may be formed in the air supply button 14, and a circular connection opening 89 may be formed in the air supply switching piston 50 to achieve the same effects as the above-described embodiment. Alternatively, if oblong openings are formed in both the air supply button 14 and the air supply switching piston 50, the airtightness can be further improved.

The oblong opening is not restricted to the air supply switching piston 50 or the air supply button 14, but it may be formed at other positions in members that connect and disconnect a fluid passage. The oblong opening may be formed in the water supply switching piston 48 and the base cylinder 42, for example.

Figure 13:
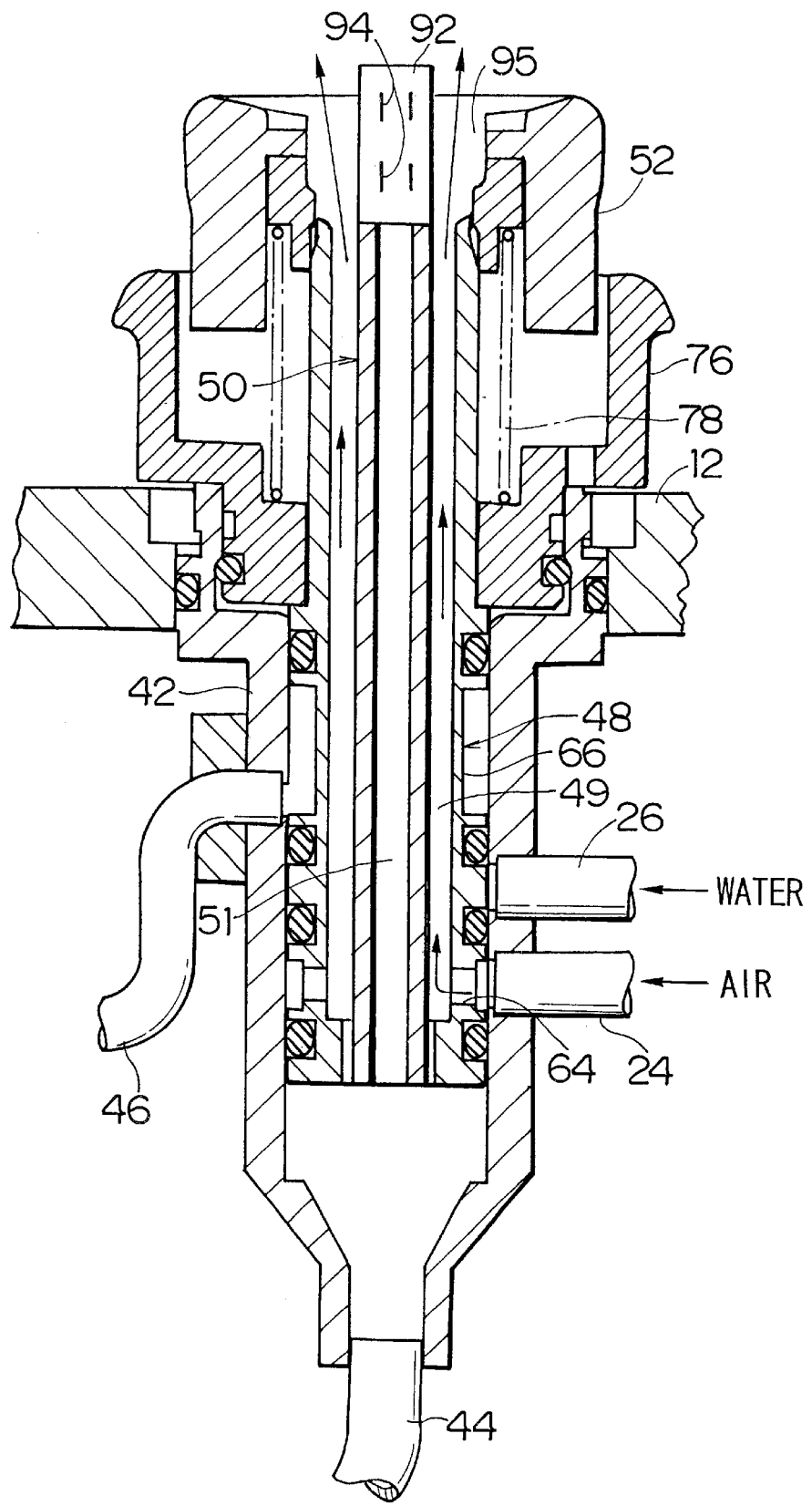
FIG. 13 is a sectional view showing the structure of an air and water supply valve structure according to the second embodiment.
Figure 14:
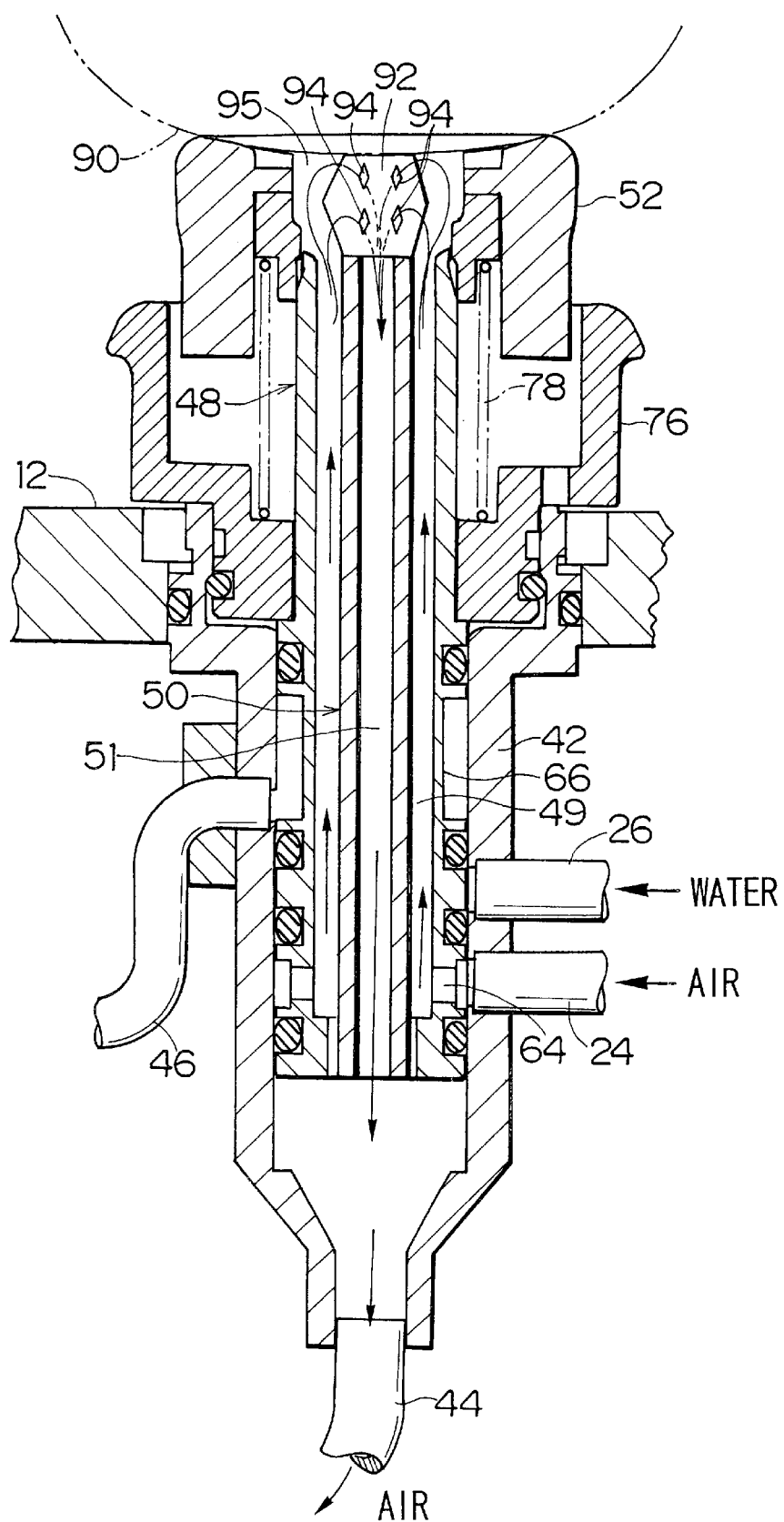
FIG. 14 is a sectional view showing a state wherein an operation member of the air and water supply valve structure in FIG. 13 is pressed by the first step.
Figure 15:
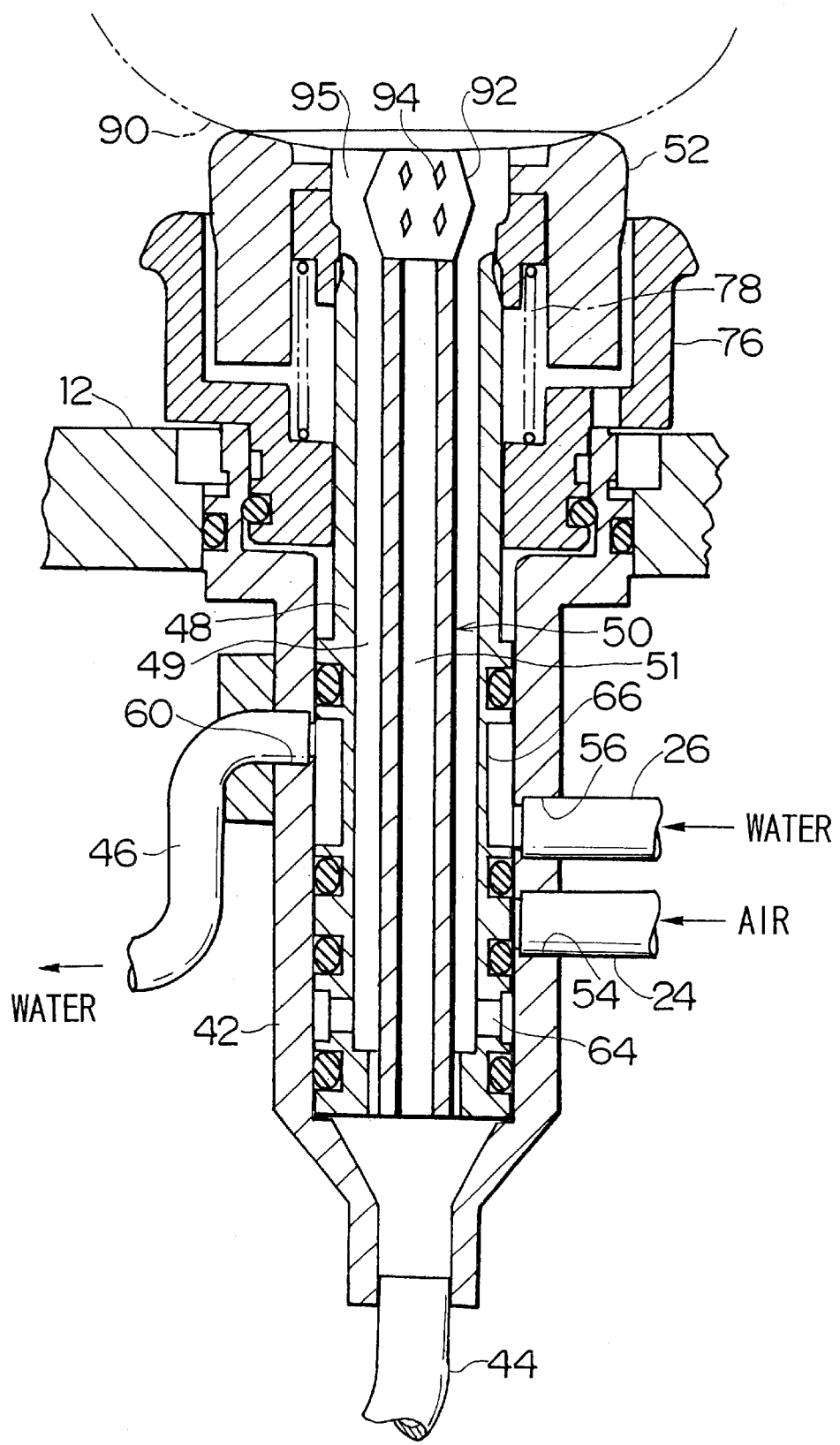
FIG. 15 is a sectional view showing a state wherein the operation member of the air and water supply valve structure in FIG. 13 is pressed by the second step.

FIGS. 13–15 are sectional views showing a valve structure of the second embodiment. Parts similar to those of the first embodiment described with reference to FIGS. 3–5 are denoted by the same reference numerals, and they will not be explained hereinbelow. The second embodiment is different from the first embodiment in that a bag-shaped elastic member (equivalent to the first operation member) 92 is provided instead of the air supply button 14.

Cut grooves 94 are formed at the circumference of the elastic member 92, and the cut grooves 94 connect to the inner space of the elastic member 92. When the elastic member 92 is not squashed as shown in FIG. 13, the cut grooves 94 are closed. When the elastic member 92 is squashed as shown in FIGS. 14 and 15, the cut grooves 94 are opened. This causes the inner space 49 of the water supply switching piston 48 and the inner space 51 of the air supply switching piston 50 to connect to one another. A pressure necessary for squashing the elastic member 92 is less than a pressure necessary for compressing the spring 78.

As shown in FIG. 14, the cut grooves 94 are opened when the elastic member 92 is squashed by the finger 90 of the operator by the first-step pressing. This connects the inner space 49 of the water supply switching piston 48 and the inner space 51 of the air supply switching piston 50. At the same time, an air leak opening 95 of the water supply button 52 is closed by the finger 90 of the operator, so that the air supplied from the air feed tube 24 into the inner space 49 can flow into the air supply tube 44 through the inner space 51 of the air supply switching piston 50 without leaking through the air leak opening 95. Consequently, the air is supplied into the body cavity.

If the water supply button 52 is pressed by the second-step pressing as shown in FIG. 15, the water supply switching piston 48 is pressed down in such a manner that the connection opening 64 of the water supply switching piston 48 is withdrawn from the port 54. This stops the supply of the air. Then, the water supply switching piston 48 is positioned in such a manner that the connection groove 66 thereof connects the port 56 and the port 60, and the water thereby flows into the water supply tube 46. Consequently, the water is supplied into the body cavity.

If the liquid flows back from the body cavity in the state wherein the elastic member 92 is not squashed as shown in FIG. 13, the backflow flows into the inner space 51 of the air supply switching piston 50. At this time, the inner space 49 of the water supply switching piston 48 and the inner space 51 of the air supply switching piston 50 are unconnected, since the elastic member 92 is not squashed, in other words, the cut grooves 94 are not open. Therefore, the backflow does not flow into the inner space 49 of the water supply switching piston 48. More specifically, the elastic member 92 functions as a check valve in the valve structure of the second embodiment, and this eliminates the necessity of providing a special check valve and reduces the pressure loss in the air supply to the minimum.

FIGS. 16–20 are sectional views showing a valve structure according to the third embodiment. Parts similar to those of the first embodiment described with reference to FIGS. 3–5 are denoted by the same reference numerals, and they will not be explained hereinbelow. The third embodiment is different from the first embodiment in that a spiral spring (equivalent to the first operation member) 114 is provided instead of the air supply button 14.

Figure 16:
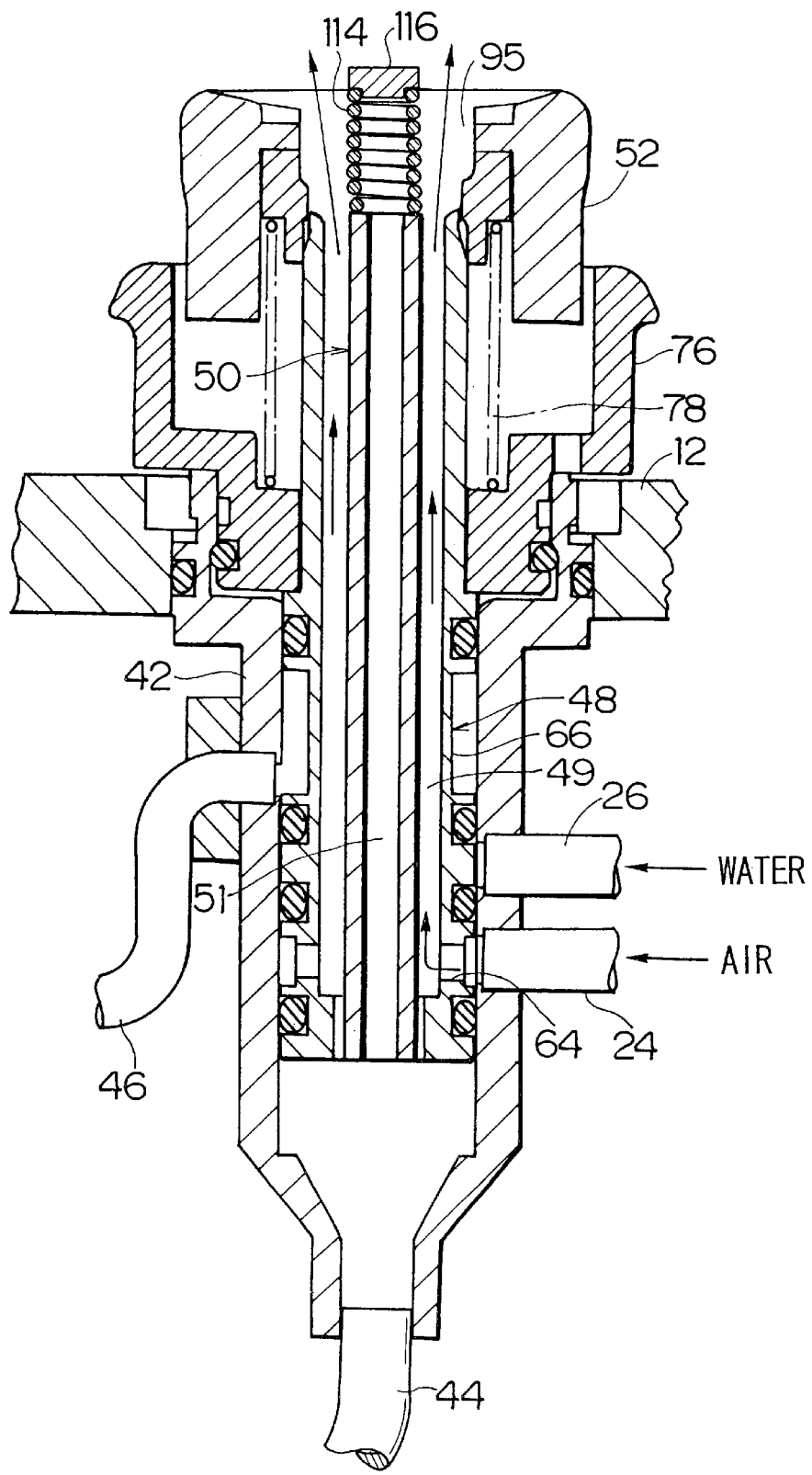
FIG. 16 is a sectional view showing the structure of an air and water supply valve structure according to the third embodiment.
Figure 17:
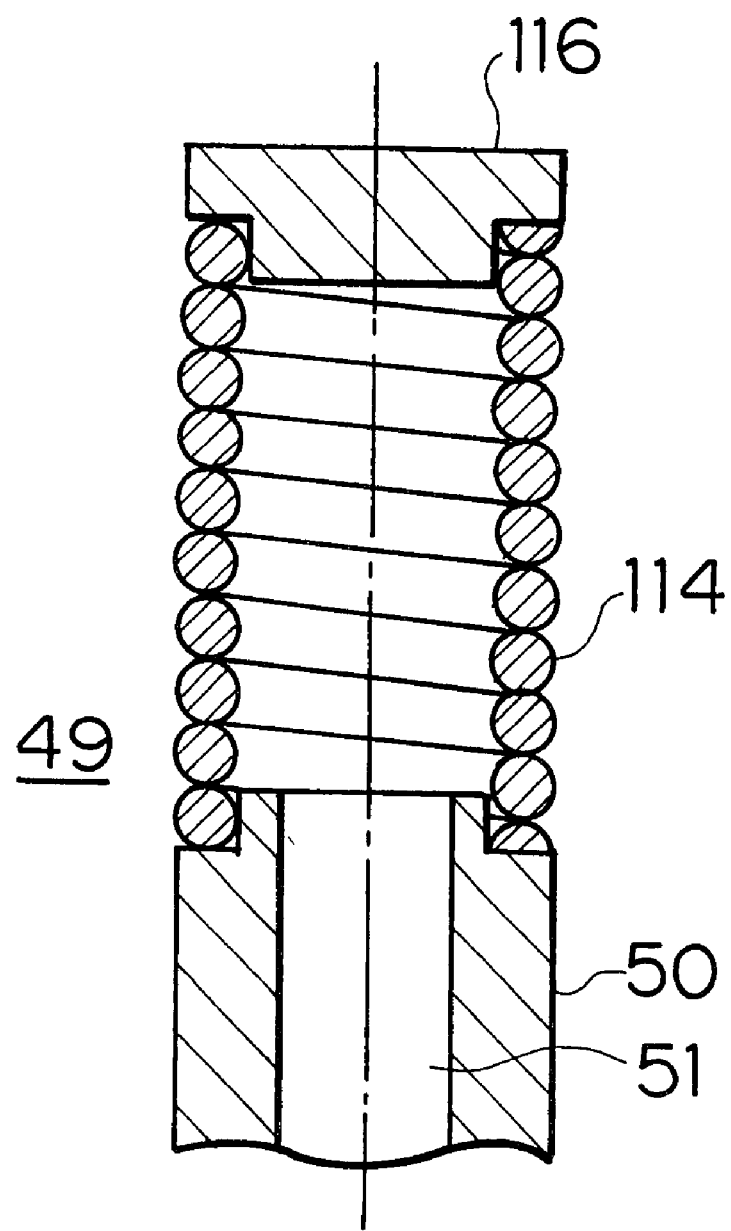
FIG. 17 is an enlarged sectional view showing the principal part of the air and water supply valve structure in the state in FIG. 16.
Figure 18:
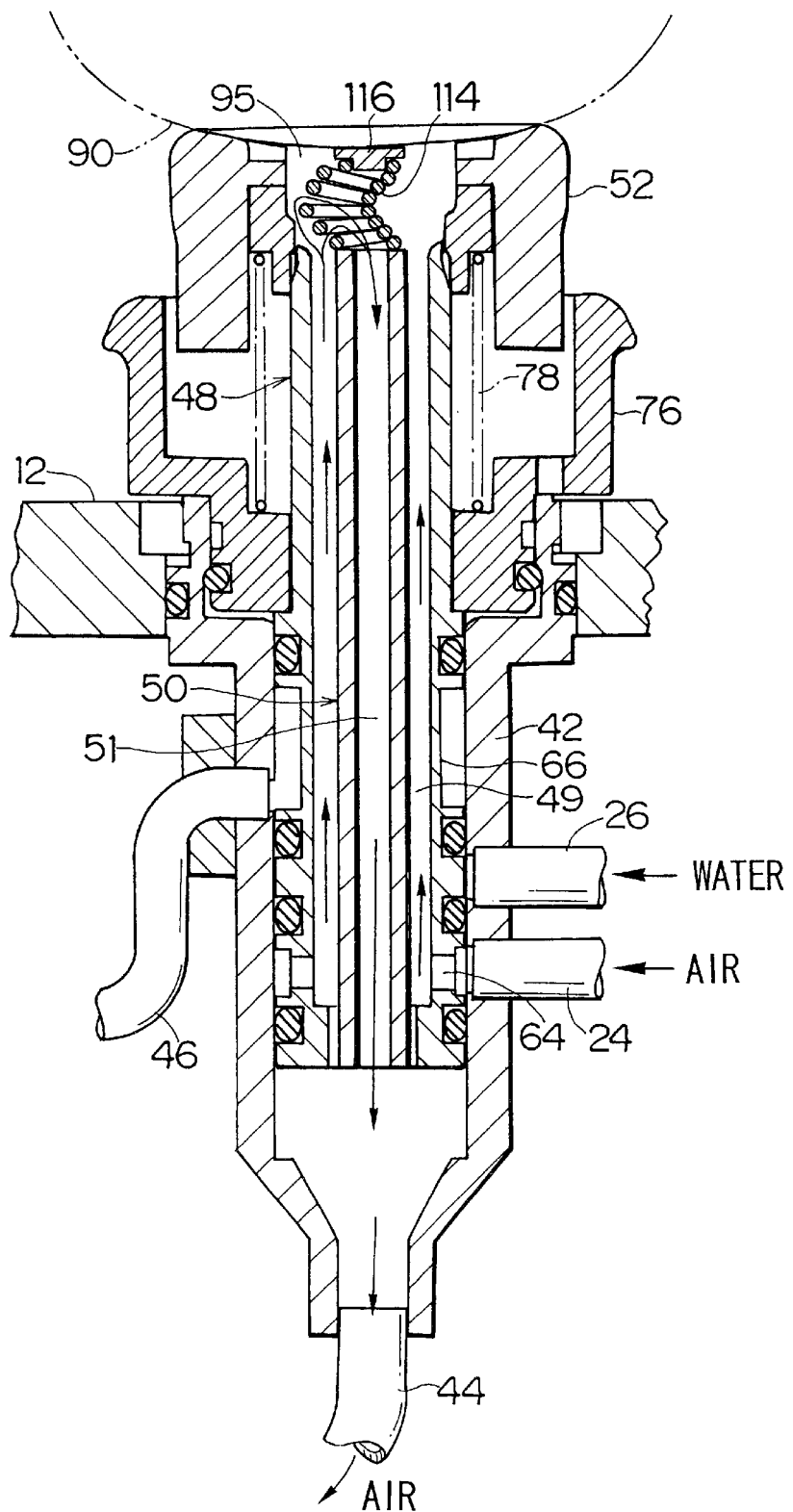
FIG. 18 is a sectional view showing a state wherein an operation member of the air and water supply valve structure in FIG. 16 is pressed by the first step.
Figure 19:
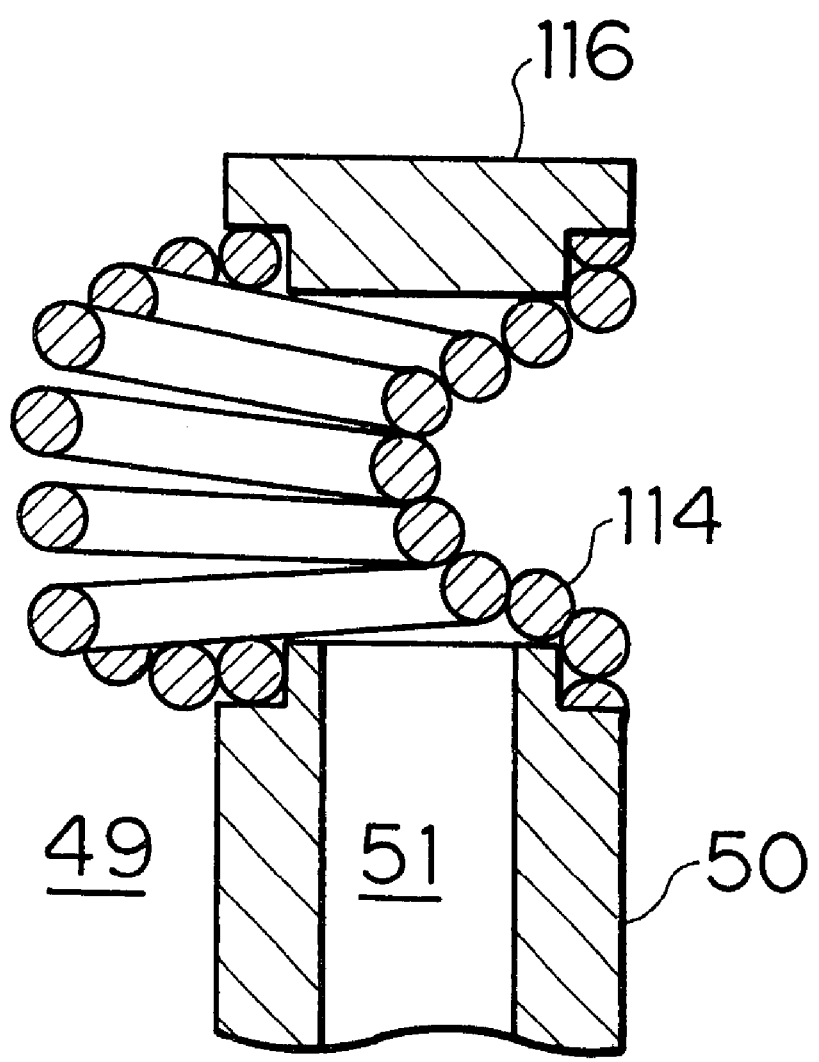
FIG. 19 is an enlarged sectional view showing the principal part of the air and water supply valve structure in the state in FIG. 18.
Figure 20:
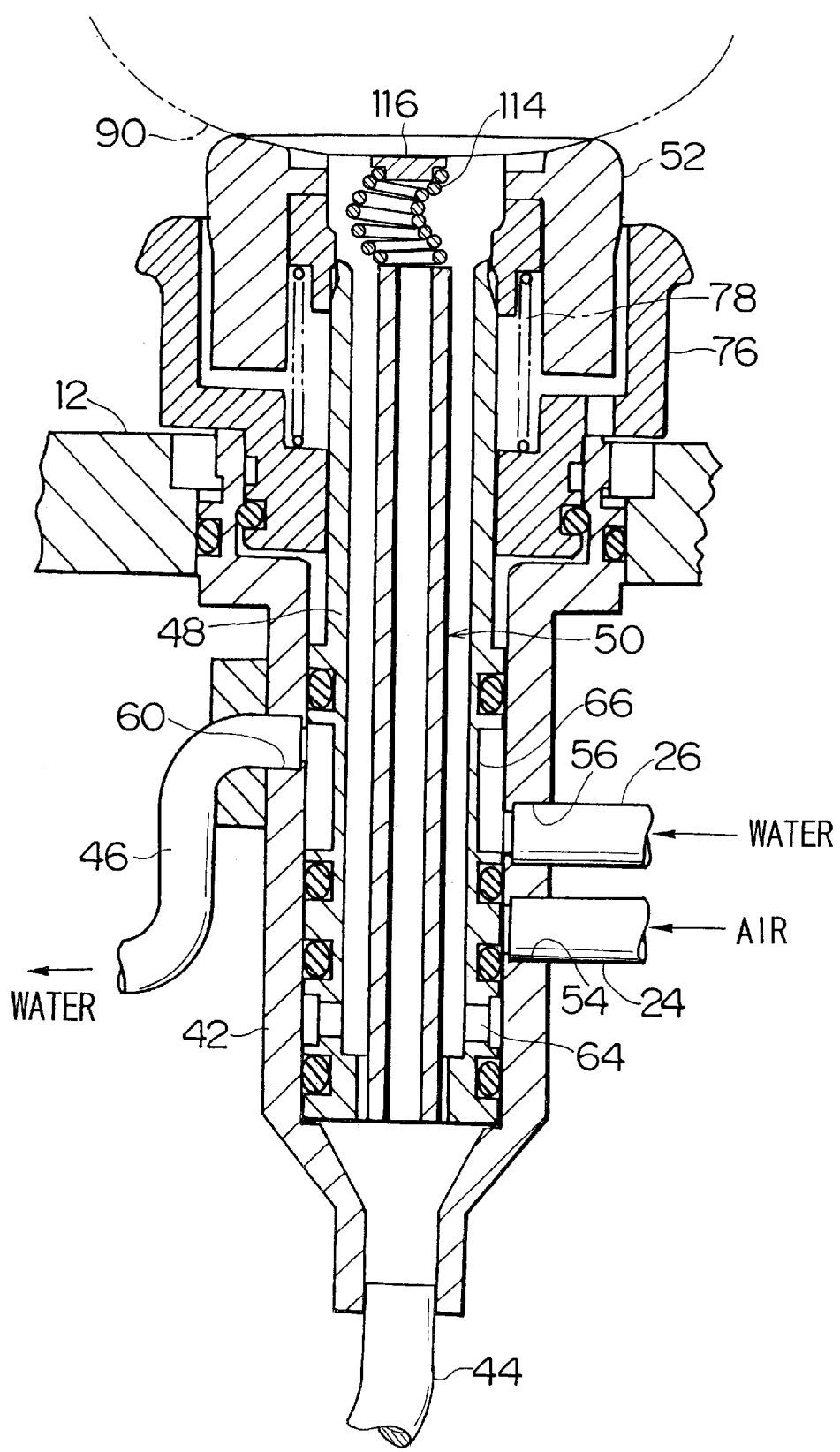
FIG. 20 is a sectional view showing a state wherein the operation member of the air and water supply valve structure in FIG. 16 is pressed by the second step.

As shown in FIG. 17, the spiral spring 114 is mounted at the end of the air supply switching piston 50, and a column-shaped lid 116 is attached to the end of the spiral spring 114. The spiral spring 114 is formed in such a manner that adjacent spirals are in close contact with one another, and therefore, the inner space 49 of the water supply switching piston 48 and the inner space 51 of the air supply switching piston 50 are unconnected in the state shown in FIGS. 16 and 17. If compressed, the spiral spring 114 is buckled as shown in FIGS. 18–20, and gaps are formed between the adjacent spirals of the spiral spring 114. This connects the inner space 49 of the water supply switching piston 48 and the inner space 51 of the air supply switching piston 50 through the gaps. A pressure necessary for buckling the spiral spring 114 is less than a pressure necessary for compressing the spring 78.

As shown in FIGS. 18 and 19, if the operator presses down the lid 116 with the finger 90 by the first-step, the spiral spring 114 is buckled to form the gaps between the adjacent spirals. Consequently, the inner space 49 of the water supply switching piston 48 connects to the inner space 51 of the air supply switching piston 50. At the same time, the air leak opening 95 of the water supply button 52 is closed by the operator's finger 90, so that the air supplied from the air feed tube 24 into the inner space 49 can flow into the air supply tube 44 through the inner space 51 of the air supply switching piston 50 without leaking through the air leak opening 95. Consequently, the air is supplied into the body cavity.

If the water supply button 52 is pressed by the second-step pressing as shown in FIG. 20, the water supply switching piston 48 is pressed down in such a manner that the connection opening 64 of the water supply switching piston 48 is withdrawn from the port 54. This stops the supply of the air. Then, the water supply switching piston 48 is positioned in such a manner that the connection groove 66 thereof connects the port 56 and the port 60, and the water thereby flows into the water supply tube 46. Consequently, the water is supplied into the body cavity.

If the liquid flows back from the body cavity in the state wherein the spiral spring 114 is not buckled as shown in FIGS. 16 and 17, the backflow flows into the inner space 51 of the air supply switching piston 50. At this time, the inner space 49 of the water supply switching piston 48 and the inner space 51 of the air supply switching piston 50 are unconnected, since the adjacent spirals of the spiral spring 114 are in close contact with one another. Therefore, the backflow does not flow into the inner space 49 of the water supply switching piston 48. More specifically, the spiral spring 114 functions as a check valve in the valve structure of the third embodiment, and this eliminates the necessity of providing a special check valve and reduces the pressure loss in the air supply to the minimum. According to the third embodiment, the spiral spring 114 serves as the valve member, and it is therefore easy to design and manufacture the valve structure.

Figure 21:
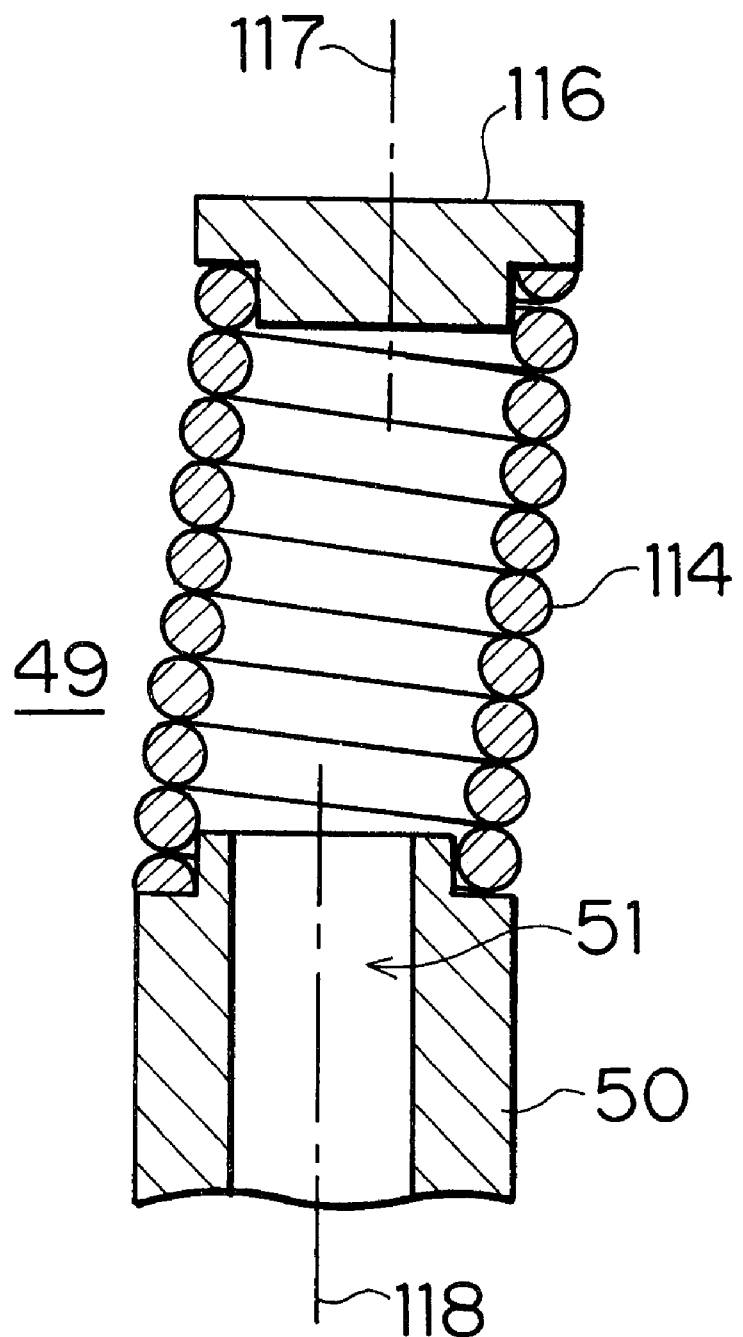
FIG. 21 is an enlarged sectional view showing the principal part of another valve structure than that in FIG. 17.
Figure 22:
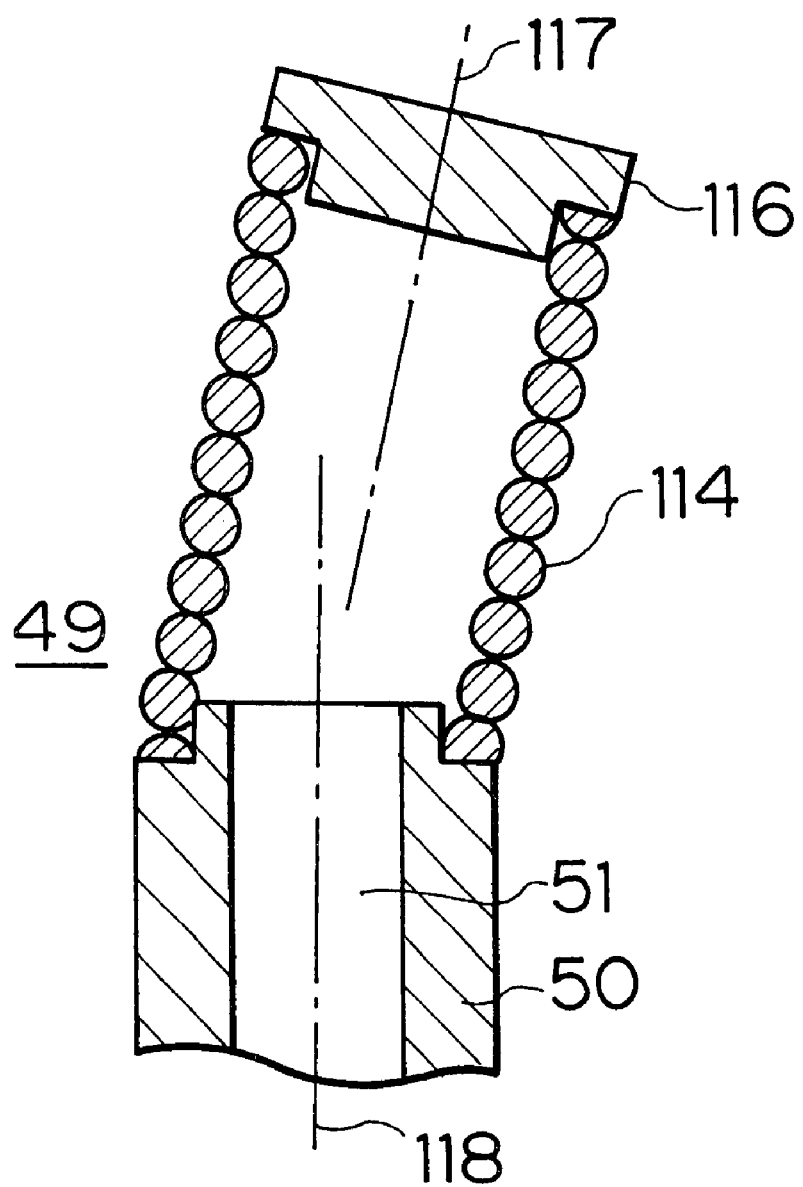
FIG. 22 is an enlarged sectional view showing the principal part of yet another valve structure than that in FIG. 17.

In FIGS. 16 and 17, the lid 116 is coaxial with the air supply switching piston 50. As shown in FIG. 21, however, the lid 116 may be arranged so that an axis 117 of the lid 116 is not coincident with but is parallel with an axis 118 of the air supply switching piston 50. Alternatively, the lid 116 may be arranged so that the axis 117 of the lid 116 is not parallel with the axis 118 of the air supply switching piston 50 as shown in FIG. 22. In these cases, the gaps are easily formed between the spirals of the spiral spring 114 when the lid 116 is pressed down, and the air is quickly supplied in response to the pressing operation of the lid 116.

FIGS. 23–26 are sectional views showing a valve structure of the fourth embodiment. Parts similar to those of the first embodiment described with reference to FIGS. 3–5 are denoted by the same reference numerals, and they will not be explained hereinbelow. The fourth embodiment is different from the first embodiment in that there is provided, instead of the air supply button 14, an operation member (equivalent to the first operation member) that is composed of a shutter plate 96, a forcing member or spring 98 and a pressing member or button 100.

Figure 24:
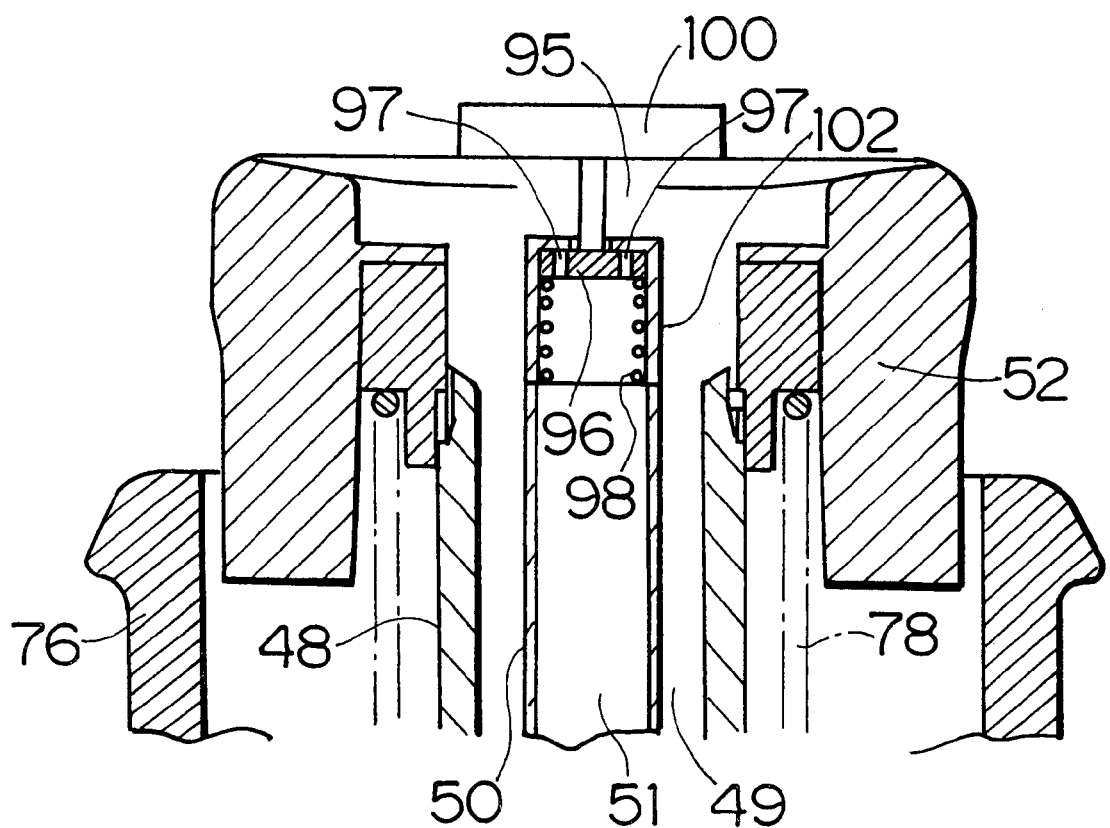
FIG. 24 is an enlarged sectional view showing the principal part of the air and water supply valve structure in FIG. 23.

The shutter plate 96 is vertically movable and is arranged in a connecting tube 102 connected to the top end of the air supply switching piston 50. The shutter plate 96 is upwardly forced by the spring 98, which has a spring constant smaller than the spring 78. As shown in FIG. 24, connection openings 97 are formed in the shutter plate 96. In FIGS. 23 and 24, the connection openings 97 are in contact with a top lid of the connecting tube 102 to be closed. Thus, the shutter plate 96 disconnects the inner space 49 of the water supply switching piston 48 and the inner space 51 of the air supply switching piston 50. On the other hand, if the shutter plate 96 is pressed down by the button 100 as shown in FIGS. 25 and 26, the inner space 49 and the inner space 51 are connected through the connection openings 97 of the shutter plate 96.

Figure 25:
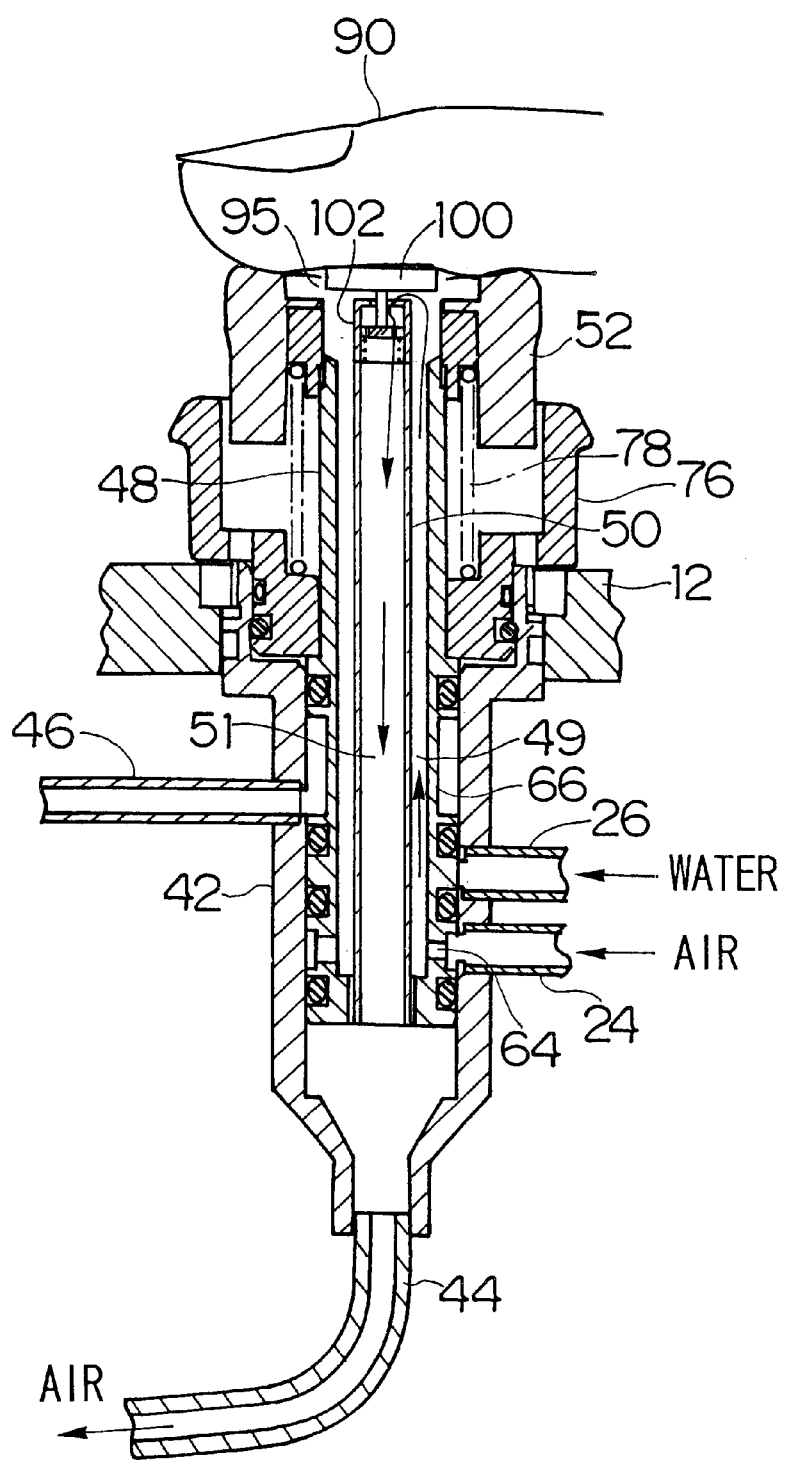
FIG. 25 is a sectional view showing a state wherein an operation member of the air and water supply valve structure in FIG. 23 is pressed by the first step.

According to the valve structure of the fourth embodiment, when the operator slightly presses the button 100 by the first step with the finger 90 as shown in FIG. 25, the shutter plate 96 is pressed down and the inner space 49 and the inner space 51 are connected with each other. At the same time, the air leak opening 95 of the water supply button 52 is closed by the operator's finger 90, so that the air supplied from the air feed tube 24 into the inner space 49 can flow into the air supply tube 44 through the inner space 51 of the air supply switching piston 50 without leaking through the air leak opening 95. Consequently, the air is supplied into the body cavity.

Figure 26:
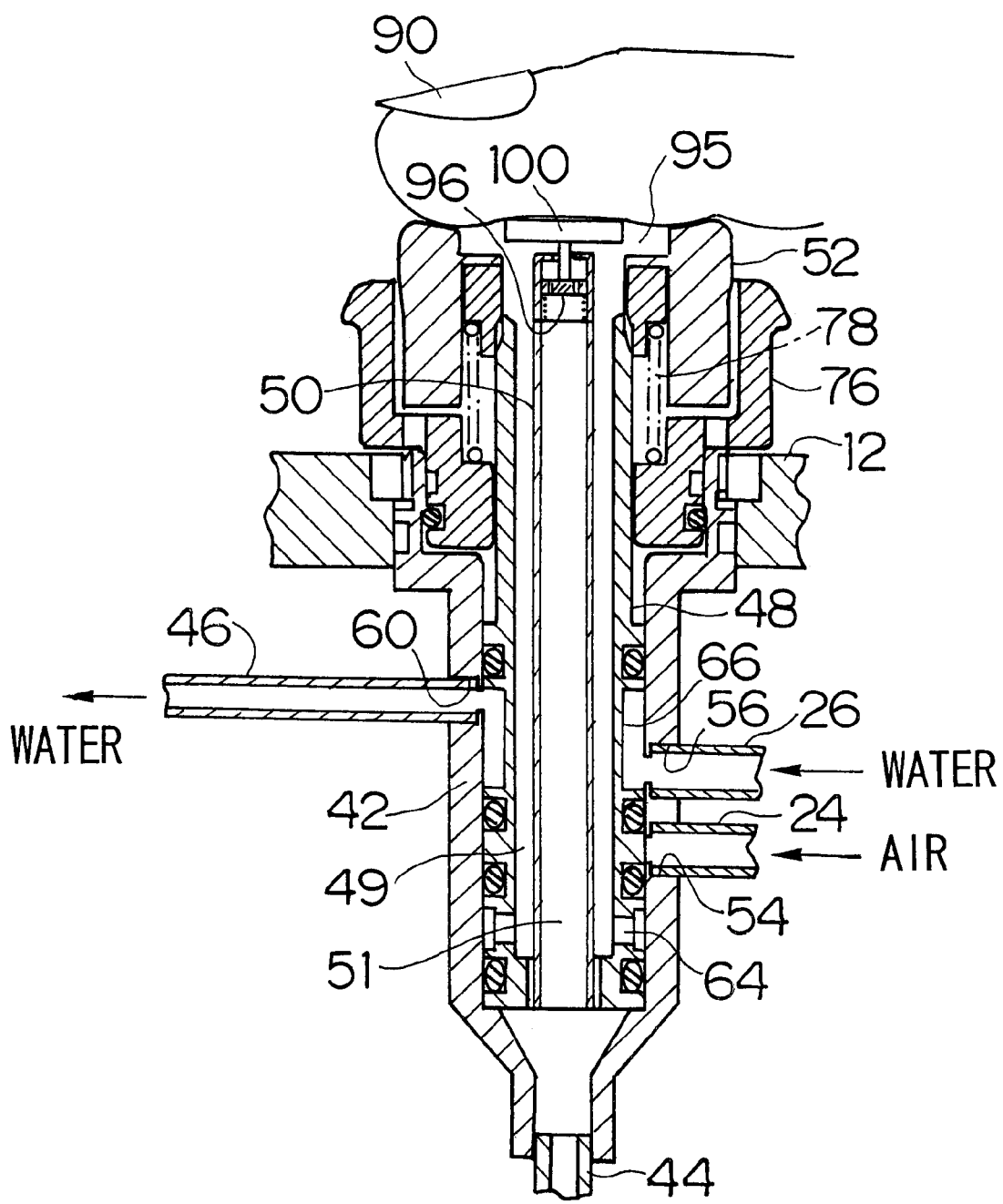
FIG. 26 is a sectional view showing a state wherein the operation member of the air and water supply valve structure in FIG. 23 is pressed by the second step.

When the water supply button 52 is pressed by the second-step pressing as shown in FIG. 26, the water supply switching piston 48 is pressed down in such a manner as to withdraw the connection opening 64 thereof from the port 54. This stops the supply of the air. Then, the water supply switching piston 48 is positioned in such a manner that the connection groove 66 thereof connects the port 56 and the port 60, and the water thereby flows into the water supply tube 46. Consequently, the water is supplied into the body cavity.

If the liquid flows back from the body cavity when the shutter plate 96 is not pressed down as shown in FIGS. 23 and 24, the backflow flows into the inner space 51 of the air supply switching piston 50. At this time, the inner space 49 of the water supply switching piston 48 and the inner space 51 of the air supply switching piston 50 are unconnected, since the connection openings 97 are closed by the shutter plate 96. Therefore, the backflow does not flow into the inner space 49 of the water supply switching piston 48. More specifically, the operation member having the shutter plate 96 functions as a check valve in the valve structure of the fourth embodiment, and this eliminates the necessity of providing a special check valve and reduces the pressure loss in the air supply to the minimum.

FIGS. 27–30 are sectional views showing the valve structure of the fifth embodiment. Parts similar to those of the first embodiment described with reference to FIGS. 3–5, and they will not be explained hereinbelow. The fifth embodiment is different from the first embodiment in that there is provided, instead of the air supply button 14, an operation member (equivalent to the first operation member) that is composed of a shutter plate 104, a forcing member or leaf spring 106 and a pressing member or button 108.

Figure 28:
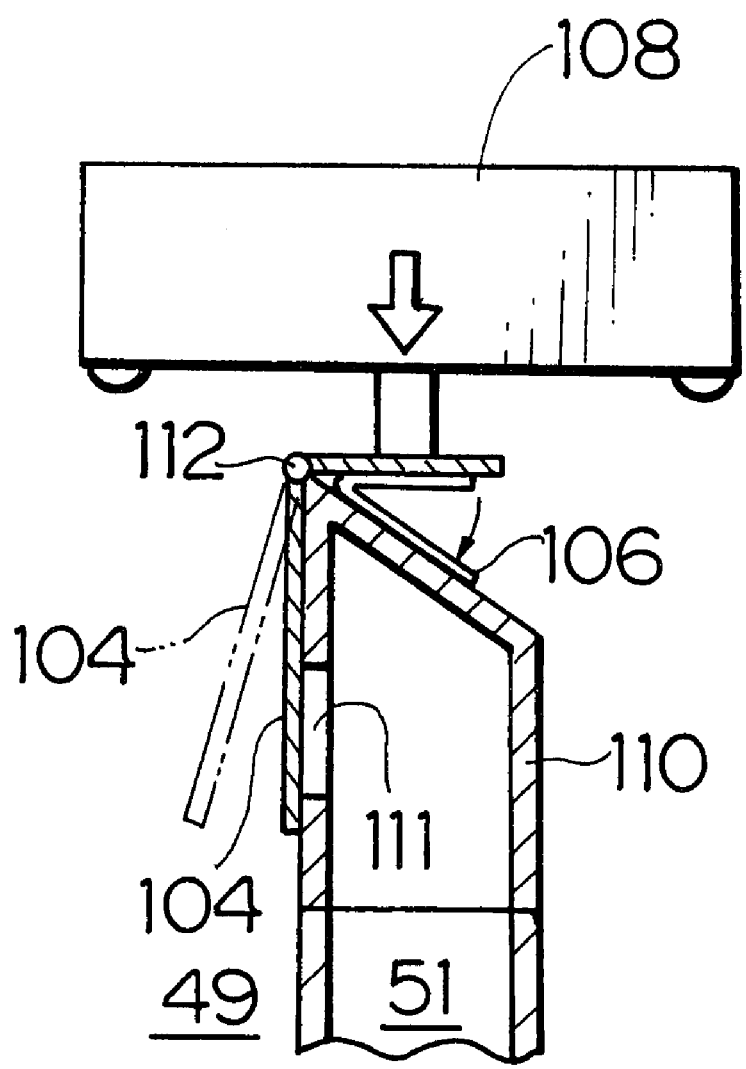
FIG. 28 is an enlarged sectional view showing the principal part of the air and water supply valve structure in FIG. 27.
Figure 29:
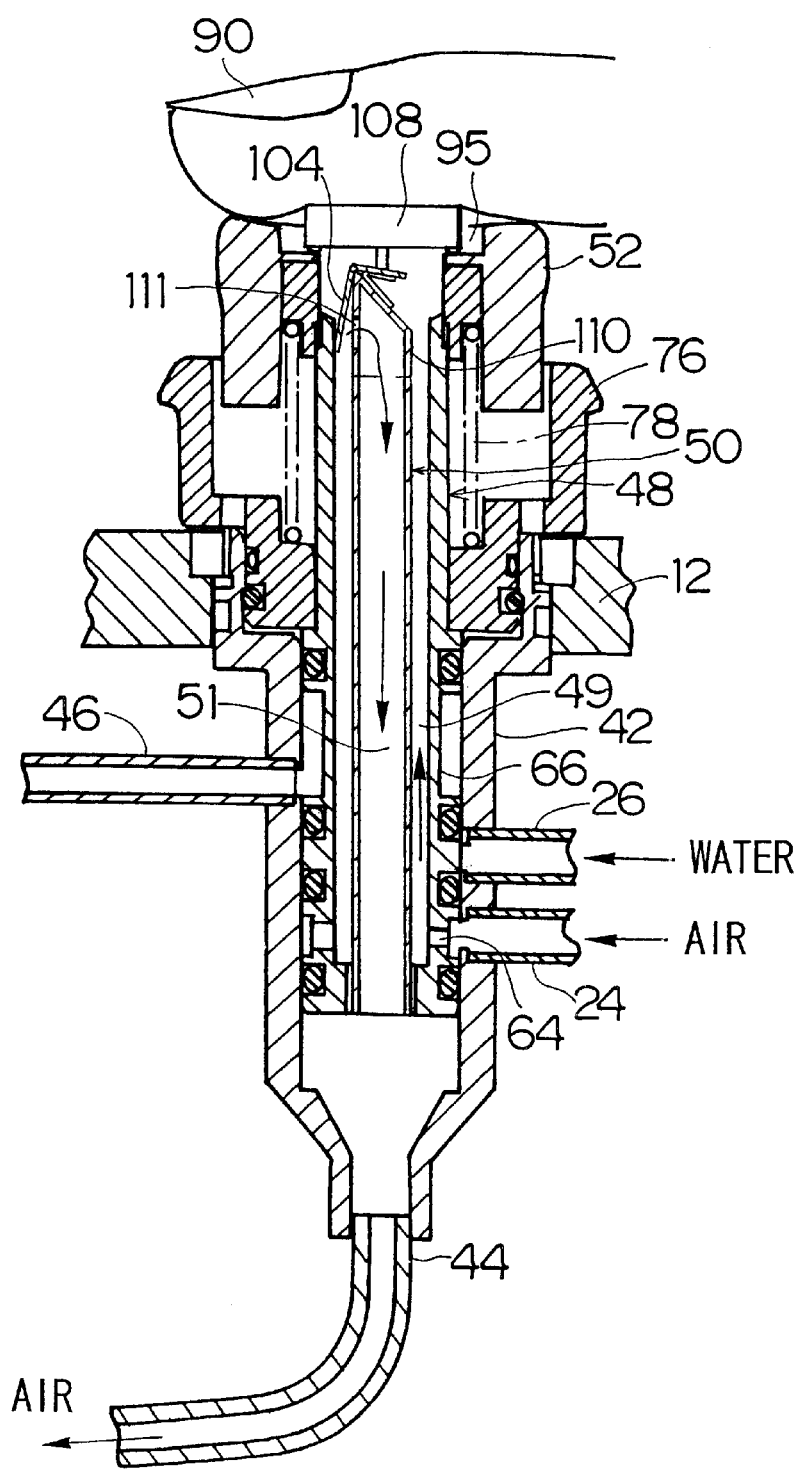
FIG. 29 is a sectional view showing a state wherein an operation member of the air and water supply valve structure in FIG. 27 is pressed by the first step.
Figure 30:
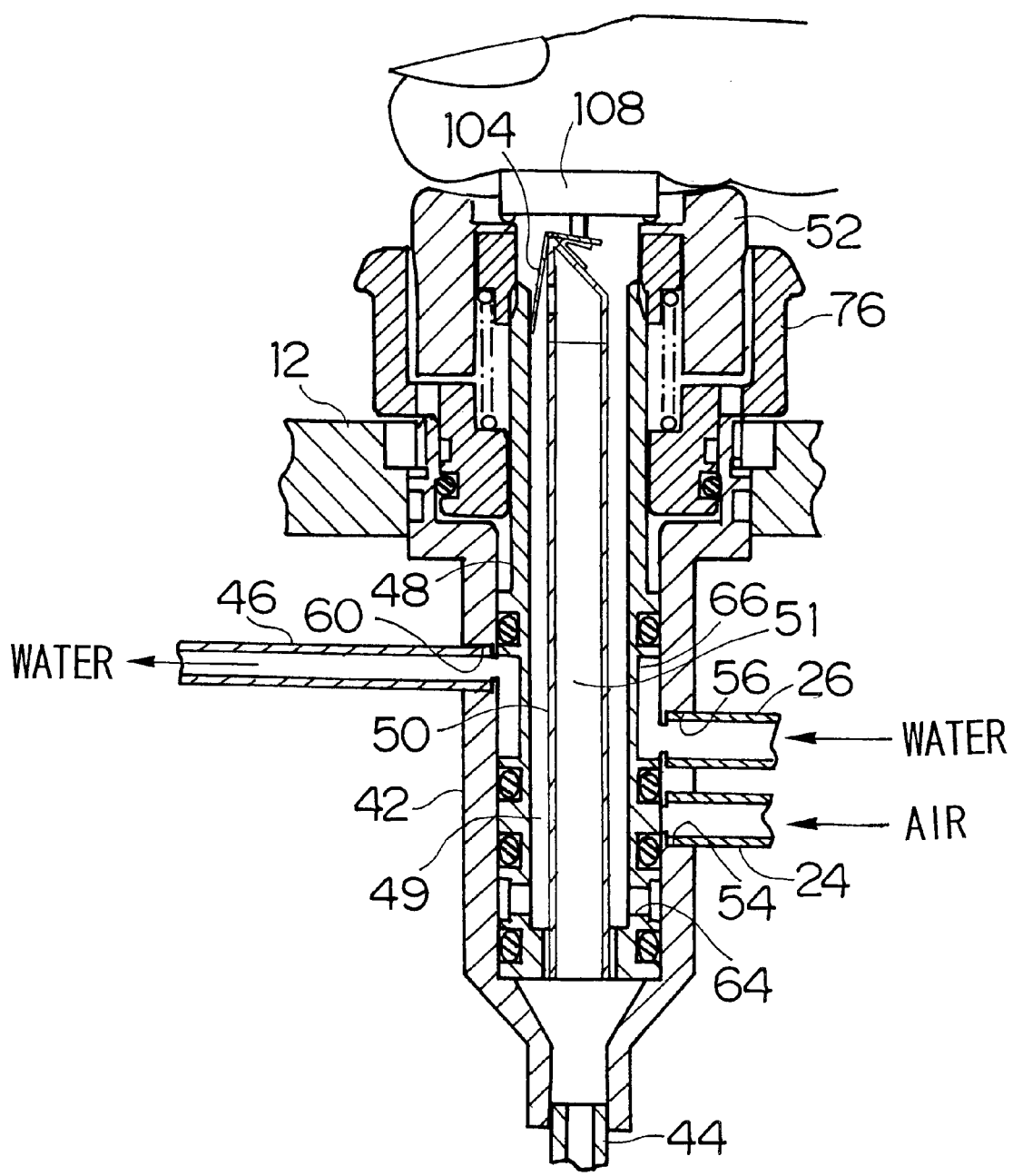
FIG. 30 is a sectional view showing a state wherein the operation member of the air and water supply valve structure in FIG. 27 is pressed by the second step.

The shutter plate 104 is inverted-L-shaped, and is swingably connected to the top of a connecting tube 110 through a pin 112 as shown in FIG. 28. The leaf spring 106 arranged between the shutter plate 104 and the connecting tube 110 forces the shutter plate 104 in such a direction as to close a connection opening 111 formed at the side of the connecting tube 110. In this state, the inner space 49 of the water supply switching piston 48 and the inner space 51 of the air supply switching piston 50 are disconnected by the shutter plate 104. On the other hand, if the button 108 is pressed down to swing the shutter plate 104 as shown in FIGS. 29 and 30, the shutter plate 104 is withdrawn from the connection opening 111, the connection opening 111 is opened, and the inner space 49 and the inner space 51 are connected through the connection opening 111 as a result. A pressure applied to the button 108 necessary for swinging the shutter plate 104 is less than a pressure necessary for compressing the spring 78.

According to the valve structure of the fifth embodiment, when the operator slightly presses the button 108 by the first step with the finger 90 as shown in FIG. 29, the shutter plate 104 swings to thereby connect the inner space 49 and the inner space 51 through the connection opening 111. At the same time, the air leak opening 95 of the water supply button 52 is closed by the operator's finger 90, so that the air supplied from the air feed tube 24 into the inner space 49 can flow into the air supply tube 44 through the inner space 51 of the air supply switching piston 50 without leaking through the air leak opening 95. Consequently, the air is supplied into the body cavity.

When the water supply button 52 is pressed by the second-step pressing as shown in FIG. 30, the water supply switching piston 48 is pressed down in such a manner as to withdraw the connection opening 64 of the water supply switching piston 48 from the port 54. This stops the supply of the air. Then, the water supply switching piston 48 is positioned in such a manner that the connection groove 66 thereof connects the port 56 and the port 60, and the water thereby flows into the water supply tube 46. Consequently, the water is supplied into the body cavity.

Figure 27:
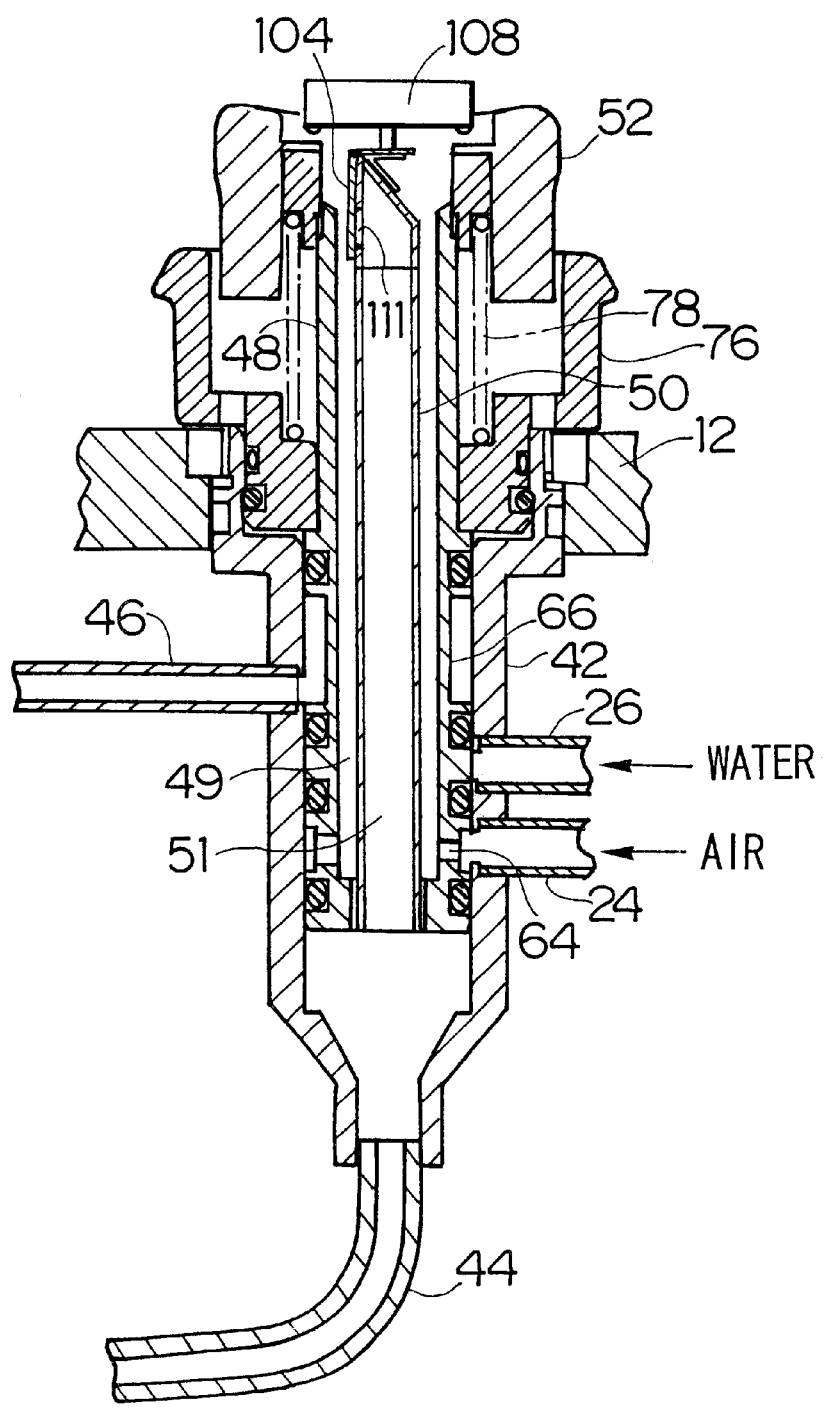
FIG. 27 is a sectional view showing the structure of an air and water supply valve structure according to the fifth embodiment.

If the liquid flows back from the body cavity when the shutter plate 104 is not swung as shown in FIG. 27, the backflow flows into the inner space 51 of the air supply switching piston 50. At this time, of the water supply switching piston 48 and the inner space 51 of the air supply switching piston 50 are unconnected, since the connection opening 111 is closed by the shutter plate 104. Therefore, the backflow does not flow into the inner space 49 of the water supply switching piston 48. More specifically, the operation member having the shutter plate 104 functions as a check valve in the valve structure of the fifth embodiment, and this eliminates the necessity of providing a special check valve and reduces the pressure loss in the air supply to the minimum. The leaf spring 104 has a relatively large spring constant so that the pressure generated by the backflow cannot swing the shutter plate 104 and cannot open the connection opening 111.

In the above-stated embodiments, the air supply button 14, the elastic member 92, the spiral spring 114 and the shutter plates 96, 104 are given as the examples of the first operation member, but any other kinds of members with the same functions as them also be used as the first operation member.

In the above-stated embodiments, the direct viewing endoscope with the eyepiece 20 provided at the hand operation part 10 is described, but the air and water supply valve structure of the present invention may be applied to an electronic endoscope.

As set forth hereinabove, according to the present invention, the first operation member functions as the check valve in the air and water supply valve structure. This eliminates the necessity of providing a special check valve and reduces the pressure loss in the air supply to the minimum.

Moreover, the button, the elastic member or the shutter plate is used as the first operation member, and this enables the air to flow into the air supply tube without any resistance and reduces the pressure loss in the air supply to the minimum.

Further, the air supply tube and the water supply tube are straight, and this facilitates the cleaning of the air supply tube and the water supply tube since the cleaning brush can easily be inserted into them.

Furthermore, the opening of one of the two slidable members in the valve structure has a shorter side in the sliding direction and a longer side in the direction perpendicular to the sliding direction. This improves the airtightness of the fluid passage without increasing the stroke length of the slidable members.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An air and water supply valve structure provided at a manual operation part of an endoscope, comprising:
    a base cylinder that is a hollow cylinder connecting: to an air feed tube feeding air into the base cylinder, to a water feed tube feeding water into the base cylinder, to an air supply tube to supply the air from the base cylinder to an air and water supply opening formed at an end of an insertion part of the endoscope, and to a water supply tube to supply the water from the base cylinder to the air and water supply opening;
    a first piston that is a hollow cylinder slidably inserted into the base cylinder, the first piston having a connection opening to connect the air feed tube and an inner space of the first piston, the first piston having a connection passage to connect the water feed tube and the water supply tube;
    a second piston that is a hollow cylinder arranged inside the first piston, an inner space of the second piston being connected to the air supply tube;
    a first operation member provided to the second piston, the first operation member being pressed by first and second steps, the first operation member connecting, when pressed by the first step, the inner space of the first piston and the inner space of the second piston, and the first operation member disconnecting, when not pressed, the inner space of the first piston and the inner space of the second piston; and
    a second operation member provided to the first piston, wherein when the first operation member is pressed by the second step, the second operation member is pressed and positions the first piston such that the connection opening of the first piston is disconnected from the air feed tube and that the connection passage of the first piston connects the water feed tube and the water supply tube.

2. The air and water supply valve structure as defined in claim 1, wherein the first operation member comprises a button with a connection opening to connect the inner space of the first piston and the inner space of the second piston.

3. The air and water supply valve structure as defined in claim 1, wherein:
    the first operation member comprises a bag-shaped elastic member around which a cut groove is formed;
    when the bag-shaped elastic member is not pressed, the cut groove is closed to disconnect the inner space of the first piston and the inner space of the second piston; and
    when the bag-shaped elastic member is pressed by the first step, the bag-shaped elastic member is deformed and the cut groove is opened to connect the inner space of the first piston and the inner space of the second piston.

4. The air and water supply valve structure as defined in claim 1, wherein:
    the first operation member comprises a spiral spring having adjacent spirals;
    when the spiral spring is not pressed, the adjacent spirals are in close contact with one another to disconnect the inner space of the first piston and the inner space of the second piston; and
    when the spiral spring is pressed by the first step, the spiral spring is buckled and gaps are formed between the adjacent spirals to connect the inner space of the first piston and the inner space of the second piston.

5. The air and water supply valve structure as defined in claim 1, wherein the first operation member comprises:
    a shutter plate provided at an opening to connect the inner space of the first piston and the inner space of the second piston, the shutter plate opening and closing the opening when operated;
    a forcing member that forces the shutter plate in such a direction as to close the opening; and
    a pressing member that presses the shutter plate against the force of the forcing member in such a direction as to open the opening.

6. The air and water supply valve structure as defined in claim 1, wherein the air supply tube and the water supply tube are straight over predetermined lengths, respectively.

7. The air and water supply valve structure as defined in claim 1, wherein the air supply tube is straight and arranged parallel to an axial direction of the base cylinder over a predetermined length, the air supply tube having a mouth thereof within an inner diameter of the base cylinder.

8. A valve structure in an endoscope, comprising:
    a first member having a first passage for a fluid, the first passage having a first opening; and
    a second member having a second passage for the fluid, the second passage having a second opening;
    wherein the first and second members are slidable with respect to one another in a sliding direction, the first and second passages are connected through the first and second openings when the first and second openings are faced to one another, the first and second passages are disconnected when the first and second openings are not faced to one another, and at least one of the first and second openings has a length thereof in the sliding direction being shorter than a length thereof in a direction perpendicular to the sliding direction.

* * * * *